(12) United States Patent
Huberman

(10) Patent No.: US 9,511,070 B2
(45) Date of Patent: Dec. 6, 2016

(54) HETEROCYCLYL CARBOXAMIDES FOR TREATING VIRAL DISEASES

(71) Applicant: NOVADRUG, LLC, Chicago, IL (US)

(72) Inventor: Eliezer Huberman, Chicago, IL (US)

(73) Assignee: NovaDrug, LLC, Chicago, IL (US)

( * ) Notice: Subject to any disclaimer, the term of this patent is extended or adjusted under 35 U.S.C. 154(b) by 0 days.

(21) Appl. No.: 14/422,543

(22) PCT Filed: Aug. 30, 2013

(86) PCT No.: PCT/US2013/057585
§ 371 (c)(1),
(2) Date: Feb. 19, 2015

(87) PCT Pub. No.: WO2014/036443
PCT Pub. Date: Mar. 6, 2014

(65) Prior Publication Data
US 2015/0238489 A1 Aug. 27, 2015

Related U.S. Application Data

(60) Provisional application No. 61/695,869, filed on Aug. 31, 2012, provisional application No. 61/779,595, filed on Mar. 13, 2013.

(51) Int. Cl.
*A61K 31/445* (2006.01)
*A61K 31/44* (2006.01)
*A61K 31/519* (2006.01)
(Continued)

(52) U.S. Cl.
CPC ............ *A61K 31/519* (2013.01); *A61K 31/445* (2013.01); *A61K 31/45* (2013.01); *A61K 31/454* (2013.01); *A61K 31/4545* (2013.01);
(Continued)

(58) Field of Classification Search
CPC . A61K 31/45; A61K 31/454; A61K 31/4709
USPC .................. 514/317, 314, 322, 321, 316
See application file for complete search history.

(56) References Cited

U.S. PATENT DOCUMENTS 2,792,399 A 5/1957 Ekenstam et al.
2005/0053625 A1 3/2005 Block et al.
(Continued)

FOREIGN PATENT DOCUMENTS

EP 2412706 2/2012
JP 2005-500288 1/2005
(Continued)

OTHER PUBLICATIONS

Nies et al. Goodman & Gilman's the pharmacological Basis of Therapeutics, Ninth Edition, 1996, pp, 51, 57 and 58.*
(Continued)

*Primary Examiner* — Shengjun Wang
(74) *Attorney, Agent, or Firm* — Barnes & Thornburg LLP; Alice O. Martin

(57) ABSTRACT

Methods, uses, medicaments, and unit doses for treating viral diseases are described herein. The methods, uses, medicaments, and unit doses include (a) substituted piperidine and piperazine carboxamides, or a pharmaceutically acceptable salt thereof and (b) one or more pharmaceutically acceptable carriers, excipients or diluents, or combinations thereof. Viral diseases include hepatitis C virus, HIV, BVDV, and Coronavirus infections.

13 Claims, 8 Drawing Sheets

(51) Int. Cl.
| | |
|---|---|
| *A61K 31/45* | (2006.01) |
| *A61K 31/496* | (2006.01) |
| *A61K 31/4709* | (2006.01) |
| *A61K 31/497* | (2006.01) |
| *A61K 31/454* | (2006.01) |
| *A61K 31/4545* | (2006.01) |
| *A61K 31/506* | (2006.01) |

(52) U.S. Cl.
CPC ......... *A61K31/4709* (2013.01); *A61K 31/496* (2013.01); *A61K 31/497* (2013.01); *A61K 31/506* (2013.01)

(56) References Cited

U.S. PATENT DOCUMENTS

| | | |
|---|---|---|
| 2005/0250677 A1 | 11/2005 | Balzarini et al. |
| 2011/0319412 A1 | 12/2011 | Sakagami et al. |

FOREIGN PATENT DOCUMENTS

| | | |
|---|---|---|
| JP | 2008-516897 | 1/2005 |
| WO | WO 99/42455 | 8/1999 |
| WO | WO 02/43734 | 6/2002 |
| WO | WO 02/100851 | 12/2002 |
| WO | WO 2004/108719 | 12/2004 |
| WO | WO 2006/014012 | 2/2006 |
| WO | WO 2006/074025 | 7/2006 |
| WO | WO 2006/135993 | 12/2006 |
| WO | WO 2009/010480 | 1/2009 |
| WO | WO 2010/141738 | 12/2010 |
| WO | WO 2011/060026 | 5/2011 |
| WO | WO 2011/060396 | 5/2011 |
| WO | WO 2011/087738 | 7/2011 |
| WO | WO 2011/091152 | 7/2011 |
| WO | WO 2011/147753 | 12/2011 |
| WO | WO 2013/116491 | 8/2013 |

OTHER PUBLICATIONS

De Amici et al., "Antiviral activity of local anaesthetic agents," *J. Antimicrob. Chemo.*, 37: 635 (1996).

Dessalew, "QSAR Study on Piperidinecarboxamides as Antiretroviral Agents: An Insight Into the Structural Basis for HIV Coreceptor Antagonist Activity," *QSAR & Combinatorial Sci.*, 27(7): 901-912 (2008).

Du et al., "Neuropeptide Y Has a Protective Role During Murine Retroviurs-Induced Neurological Disease," *J Virol.*, 84(21): 1176-11088 (2010).

Duffy, "Synthesis and Activity of Novel HIV Protease Inhibitors with Improved Potency Against Multiple PI-Resistant Viral Strains," *Bioorganic & Medicinal Chemistry Letters*, 12: 2423-2426 (2002).

Jang et al., "Discovery of Hepatitis C Virus NS3 Helicase Inhibitors by a Multiplexed, High-Throughput Helicase Activity Assay Based on Graphene Oxide," *Angewandte Chemi Int'l. Ed.*, 52(8):2340-2344 (2013).

Search Report & Written Opinion issued in App. No. PCT/US2013/057585 (2014).

Supplementary Search Report issued in App. No. PCT/US2013/057585 (2015).

Cheng et al. "Pyridin Carboxamides: Potent Palm Site Inhibitors of HCV NS5B Polymerase," *ACS Med. Chem. Lett.*, 1(9): 466-71 (Dec. 2010).

Sindac et al., "Novel Inhibitors of Neurotropic Alphavirus Replication That Improve Host Survival in a Mouse Model of Acture Viral Encephalitis," *J. Med. Chem.*, 55(7):3535-45 (Apr. 2012).

Office Action issued in App. No. JP2015-530102 (Jan. 27, 2016).

* cited by examiner

SEQUENCE LISTING

<160> NUMBER OF SEQ ID NOS: 19

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tcaagtgagt gcccggtt                                                 18

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
agctccggtt tctctttcgc t                                             21

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tgacttcaac agcgacaccc act                                           23

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
accaccctgt tgctgtagcc aaat                                          24

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aactagggaa cccactgctt aag                                           23

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cccacaaatc aaggatatct tgtc                                          24

```
<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tccttggcac ttatctggga cgat                                          24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tcccagaagt tccacaatcc tcgt                                          24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
acgaggattg tggaacttct ggga                                          24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tggcattgag caagctaaca gcac                                          24

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
agagaaggct ttcagcccag aagt                                          24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tgcactggat gcactctatc ccat                                          24
```

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aggtttagga ttcgtgctca t                                          21

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
caccctatca ggcagtacca caaggcc                                    27

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tgcggaaccg gtgagtaca                                             19

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gaaggtgaag gtcggagtc                                             19

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gaagatggtg atgggatttc                                            20

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tctgcggaac cggtgagta                                             19

```
<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tcaggcagta ccacaaggc                                                 19
```

HETEROCYCLYL CARBOXAMIDES FOR TREATING VIRAL DISEASES

CROSS REFERENCE TO RELATED APPLICATIONS

This patent application is a U.S. nationalization under 35 U.S.C. §371 of International Application No. PCT/US2013/057585, filed Aug. 30, 2013, which claims the benefit of priority under 35 U.S.C. §119(e) to U.S. Provisional Application No. 61/695,869, filed Aug. 31, 2012, and Provisional Application No. 61/779,595, filed Mar. 13, 2013. The disclosures set forth in the referenced applications are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Aug. 29, 2013, is named 701867_SEQ_ST25.txt and is 4,573 bytes in size.

TECHNICAL FIELD

The invention described herein pertains to substituted piperidine and piperazine carboxamides and methods for their use in the treatment of viral diseases. Viral diseases include hepatitis C virus, HIV, BVDV, and Coronavirus infections.

BACKGROUND AND SUMMARY

Hepatitis C (HCV) belongs to the Flaviviridae family of positive-sense, single-stranded RNA viruses. The HCV genome encodes a polyprotein of about 3000 amino acid residues, which is processed into both structural and non-structural proteins. HCV infection is a significant global health issue; the World Health Organization estimates that over 170 million people carry the HCV infection, which can ultimately result in chronic hepatitis, cirrhosis, and hepatocellular carcinoma. It has been reported that those complications are responsible for about 10,000-20,000 deaths annually in the U.S. alone, and that HCV is the leading cause of advanced liver disease and the leading underlying cause for liver transplantation. Current therapies for HCV infection rely on the combination of interferon-α (IFN) and ribavirin. This treatment regimen reportedly causes undesirable side effects such as leucopenia, thrombocytopenia, and hemolytic anemia, with the added disadvantage that only about 50% of patients achieve a sustained viral response. Recently, new protease inhibitor drugs, namely Vertex's telaprevir and Merck's boceprevir, were added to the ribavirin and IFN combination, which were each found to shorten the treatment time and significantly increase the percentage of patients achieving a sustained viral response. However, the problem of ribavirin and IFN toxicity is still a serious setback. (see, for example, Hanazaki, Curr. Med. Chem.: Anti-Infect. Agents 2003, 2, 103; Lauer & Walker, N. Engl. J. Med. 2001, 345, 41; Gordon &. Keller, J. Med. Chem. 2005, 48, 1; Tan et al., Nat. Rev. Drug Discovery 2002, 1, 867; Idno & Bellobuono, Curr. Pharm. Des. 2002, 8, 959; Di Bisceglie et al., Hepatology 2002, 35, 224; Samuel, Clin. Microbiol. Rev. 2001, 14, 778; Klibanov et al., 2011, Pharmacotherapy 31, 951; Kwo & Zhao 2011, Clink Liver Dis. 15, 537; the foregoing publications, and each additional publication cited herein, are incorporated herein by reference). Thus, more effective and less toxic anti-HCV therapeutics are greatly needed.

Another member of the Flaviviridae family of positive-sense, single-stranded RNA viruses is the Bovine Viral Diarrhea Virus (BVDV). Infection with this virus brings about a severe mucosal disease in cattle and other ruminants as well as pigs. BVDV cattle infections are marked by nose, mouth and gastrointestinal mucosa ulceration, which cause continuous salivation, nasal discharge, coughing and/or diarrhea. As a result there is a quick virus spread among animals. The virus also causes calves to be still born, become persistently infected, or suffer growth retardation and/or display severe neurological malformations. The economic impact of BVDV is considerable, although it is difficult to precisely estimate its level since certain infections remain undiagnosed or the losses are not recognized as being due to the virus. (see, for example, Buckwold et al., Antivirus Research 2003, 60, 1; Finkielsztein et al., 2010, Current Medicinal Chemistry 17, 2933). Other members of this Flaviviridae family of diseases include West Nile Virus and Dengue Fever. Thus effective therapeutics will be useful for reducing the economic impact of BDVD, West Nile Virus and Dengue Fever.

Acquired immune deficiency syndrome (AIDS) (1) is a disease brought about by a retrovirus termed human immunodeficiency virus (HIV), which belongs to Retroviridae and Lentivirus families. This condition causes a gradual decline of the immune system and leaves the HIV-infected individuals susceptible to opportunistic infections and to tumor formation that eventually leads to death. To alleviate these devastating ills the pharmaceutical community came up with an active antiretroviral therapy. It involves a cocktail of HIV protease and reverse transcriptase inhibitor drugs. This therapy brings about a significant improvement in the general health and quality of life of many HIV-infected individuals. This recovery is also associated with a marked reduction in HIV-associated morbidity and mortality. Yet, the HIV protease and reverse transcriptase inhibitor drug cocktail does not cure the patient of the HIV infection nor does it prevent the return of AIDS, once the treatment is stopped. Thus, patients who withdraw from the therapy do not benefit from the treatment. Moreover, for a considerable fraction of AIDS patients this treatment achieves far less than optimal results because the therapy intolerance, therapy side effects or infection with a drug-resistant HIV strain. To overcome these limitations, there is a need for additional effective anti-HIV drugs, and in particular, anti-HIV drugs that are less toxic. (see, for example, Sepkowitz 2001, N. Engl. J. Med. 344, 1764; Weiss 1993, Science 260, 1273; Dybul et al. 2002, Ann. Intern. Med. 137, 381; Martinez-Picado et al. 2000, Proc. Natl. Acad. Sci. U.S.A. 97, 10948.

Another family of RNA viruses are the coronaviruses, which are species of virus belonging to the subfamily Coronavirinae in the family Coronaviridae. Coronaviruses are enveloped viruses with a positive-sense RNA genome and with a nucleocapsid of helical symmetry. Coronaviruses primarily infect the upper respiratory and gastrointestinal tract of mammals and birds. Four to five different currently known strains of coronaviruses infect humans. One of the more well-known strains of human coronavirus is SARS-CoV, which causes severe acute respiratory syndrome (SARS). Coronaviruses are also reported to cause a significant percentage of all common colds in humans. Coronaviruses are also reported to cause pneumonia, either direct viral pneumonia or a secondary bacterial pneumonia. Recently, Middle East respiratory syndrome coronavirus (MERS-CoV), a SARS-like coronavairus, has been reported in humans. Coronaviruses also infect livestock, such as chickens. The infectious bronchitis virus (IBV) is a coronavirus that targets not only the respiratory tract but also the uro-genital tract in chickens. The virus can also spread to different organs throughout the chicken.

Coronaviruses reportedly cause a range of diseases in farm animals and domesticated pets, including porcine coronavirus (transmissible gastroenteritis coronavirus, TGE), bovine coronavirus, each of which result in diarrhea in young animals, feline coronavirus, such as feline enteric coronavirus, of minor clinical significance, and feline infectious peritonitis (FIP), a disease associated with high mortality, canine coronavirus (CCoV), mouse hepatitis virus (MHV), and others. Thus, compounds, compositions and therapies are needed to treat coronavirus.

It has been discovered herein that piperidine and piperazine carboxamides, including the compounds described herein, are active antiviral agents. In particular, it has been discovered herein that piperidine and piperazine carboxamides are active anti-HIV agents. It has also been discovered herein that piperidine and piperazine carboxamides are active anti-HCV agents. It has also been discovered herein that piperidine and piperazine carboxamides are active against Flaviviridae viruses and related diseases. It has also been discovered herein that piperidine and piperazine carboxamides are active anti-BVDV agents. It has also been discovered herein that piperidine and piperazine carboxamides are active anti-West Nile virus agents. It has also been discovered herein that piperidine and piperazine carboxamides are active anti-Dengue viral agents. It has also been discovered herein that piperidine and piperazine carboxamides are active anti-coronavirus agents.

In one illustrative embodiment, described herein are substituted piperidine and piperazine carboxamides that are useful for the treatment of HIV infections, AIDS, and AIDS-related diseases. In another embodiment, described herein are pharmaceutical compositions comprising the substituted piperidine and piperazine carboxamides that are useful for the treatment of HIV infections, AIDS, and AIDS-related diseases. Illustratively, the compositions include one or more carriers, diluents, or excipients, or a combination thereof.

In another embodiment, described herein are methods for treating HIV infections, AIDS, and AIDS-related diseases, where the methods include administering the substituted piperidine and piperazine carboxamides and/or the pharmaceutical compositions including the substituted piperidine and piperazine carboxamides. In another embodiment, described herein is the use of one or more of the substituted piperidine and piperazine carboxamides and/or the pharmaceutical compositions including the substituted piperidine and piperazine carboxamides in the manufacture of a medicament for treating a patient or host animal having an HIV infection, AIDS, and AIDS-related diseases.

In another illustrative embodiment, described herein are substituted piperidine and piperazine carboxamides that are useful for the treatment of BVDV infections. In another embodiment, described herein are pharmaceutical compositions comprising the substituted piperidine and piperazine carboxamides that are useful for the treatment of BVDV infections. Illustratively, the compositions include one or more carriers, diluents, or excipients, or a combination thereof.

In another embodiment, described herein are methods for treating BVDV infections, where the methods include administering the substituted piperidine and piperazine carboxamides and/or the pharmaceutical compositions including the substituted piperidine and piperazine carboxamides. In another embodiment, described herein is the use of one or more of the substituted piperidine and piperazine carboxamides and/or the pharmaceutical compositions including the substituted piperidine and piperazine carboxamides in the manufacture of a medicament for treating a patient or host animal having a BVDV infection.

In another illustrative embodiment, described herein are substituted piperidine and piperazine carboxamides that are useful for the treatment of West Nile virus infections. In another embodiment, described herein are pharmaceutical compositions comprising the substituted piperidine and piperazine carboxamides that are useful for the treatment of West Nile virus infections. Illustratively, the compositions include one or more carriers, diluents, or excipients, or a combination thereof.

In another embodiment, described herein are methods for treating West Nile virus infections, where the methods include administering the substituted piperidine and piperazine carboxamides and/or the pharmaceutical compositions including the substituted piperidine and piperazine carboxamides. In another embodiment, described herein is the use of one or more of the substituted piperidine and piperazine carboxamides and/or the pharmaceutical compositions including the substituted piperidine and piperazine carboxamides in the manufacture of a medicament for treating a patient or host animal having a West Nile virus infection.

In another illustrative embodiment, described herein are substituted piperidine and piperazine carboxamides that are useful for the treatment of Dengue fever. In another embodiment, described herein are pharmaceutical compositions comprising the substituted piperidine and piperazine carboxamides that are useful for the treatment of Dengue fever. Illustratively, the compositions include one or more carriers, diluents, or excipients, or a combination thereof.

In another embodiment, described herein are methods for treating Dengue fever, where the methods include administering the substituted piperidine and piperazine carboxamides and/or the pharmaceutical compositions including the substituted piperidine and piperazine carboxamides. In another embodiment, described herein is the use of one or more of the substituted piperidine and piperazine carboxamides and/or the pharmaceutical compositions including the substituted piperidine and piperazine carboxamides in the manufacture of a medicament for treating a patient or host animal having a Dengue fever.

In another illustrative embodiment, described herein are substituted piperidine and piperazine carboxamides that are useful for the treatment of HCV. In another embodiment, described herein are pharmaceutical compositions comprising the substituted piperidine and piperazine carboxamides that are useful for the treatment of HCV. Illustratively, the compositions include one or more carriers, diluents, or excipients, or a combination thereof.

In another embodiment, described herein are methods for treating HCV, where the methods include administering the substituted piperidine and piperazine carboxamides and/or the pharmaceutical compositions including the substituted piperidine and piperazine carboxamides. In another embodiment, described herein is the use of one or more of the substituted piperidine and piperazine carboxamides and/or the pharmaceutical compositions including the substituted piperidine and piperazine carboxamides in the manufacture of a medicament for treating a patient or host animal having an HCV infection.

In another illustrative embodiment, described herein are substituted piperidine and piperazine carboxamides that are useful for the treatment of coronavirus infection, such as SARS-CoV and MERS-CoV infection. In another embodiment, described herein are pharmaceutical compositions comprising the substituted piperidine and piperazine carboxamides that are useful for the treatment of coronavirus infection, such as SARS-CoV and MERS-CoV infection. Illustratively, the compositions include one or more carriers, diluents, or excipients, or a combination thereof.

In another embodiment, described herein are methods for treating coronavirus infection, such as SARS-CoV and MERS-CoV infection, where the methods include administering the substituted piperidine and piperazine carboxamides and/or the pharmaceutical compositions including the substituted piperidine and piperazine carboxamides. In another embodiment, described herein is the use of one or more of the substituted piperidine and piperazine carboxamides and/or the pharmaceutical compositions including the substituted piperidine and piperazine carboxamides in the manufacture of a medicament for treating a patient or host animal having a coronavirus infection, such as a SARS-CoV or MERS-CoV infection.

In one illustrative embodiment, described herein are substituted piperidine and piperazine carboxamides that are effective in the treatment of viral diseases including HCV, BVDV, coronavirus, and/or HIV. In another embodiment, described herein are pharmaceutical compositions comprising the substituted piperidine and piperazine carboxamides, and methods for the use of the substituted piperidine and piperazine carboxamides, including pharmaceutical compositions containing them, in the treatment of viral diseases including HCV, BVDV, coronavirus and/or HIV.

In another embodiment, described herein is a pharmaceutical composition for treating a viral infection, where the composition includes (a) a therapeutically effective amount of one or more compounds of the formula

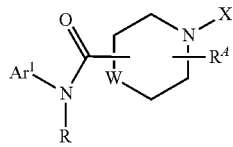

or a pharmaceutically acceptable salt, hydrate, or solvate thereof; wherein:
W is a nitrogen or a carbon;
X is alkyl, alkenyl, alkynyl, heteroalkyl, cycloalkyl, cycloheteroalkyl, arylalkyl, heteroarylalkyl, aryl or heteroaryl, each of which is optionally substituted; or acyl;
$R^4$ is hydrogen or optionally substituted alkyl;
R is H, alkyl, heteroalkyl, acyl, alkoxycarbonyl, or aminocarbonyl, each of which is optionally substituted; or R is a prodrug moiety; and
$Ar^1$ is aryl or heteroaryl, each of which is optionally substituted; and
(b) one or more pharmaceutically acceptable carriers, excipients, or diluents, or combinations thereof.

In another embodiment, described herein are methods for treating a viral infection in a patient, the methods comprising the step of administering to the patient a therapeutically effective amount of one or more of the compounds described herein, or a therapeutically effective amount of one or more of the compositions described herein, or one or more of the unit doses or unit dosage forms described herein.

In another embodiment, described herein are uses of one or more compounds or compositions described herein in the manufacture of a medicament for treating a viral infection, where the medicament includes (a) a therapeutically effective amount of one or more of the compounds or compositions described herein; and optionally, (b) one or more carriers, excipients, or diluents, or combinations thereof.

In another embodiment, described herein are compositions, methods, and uses where the viral infection is a DNA or RNA viral infection. In another embodiment, described herein are compositions, methods, and uses where the viral infection is a hepatitis C viral infection. In another embodiment, described herein are compositions, methods, and uses where the viral infection is a HIV infection. In another embodiment, described herein are compositions, methods, and uses where the viral infection is a BVDV infection. In another embodiment, described herein are compositions, methods, and uses where the viral infection is a coronavirus infection.

DETAILED DESCRIPTION

Figure 1A:
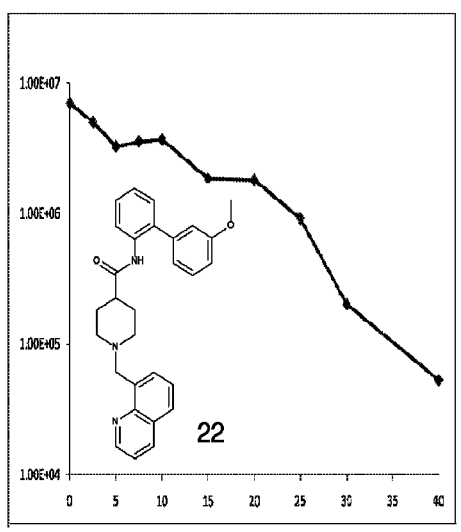
FIGS. 1A, 1B, and 1C show the intracellular HCV RNA levels for Examples 22, 24, and 28, respectively, when cultures are incubated with illustrative compounds described herein at the doses shown. Each test compound shows a dose response (μM). Without being bound by theory, it is believed herein that when HCV RNA levels are compared among the samples, the data may indicate that the test compounds cause a dose dependent decrease in HCV RNA levels relative to the mock-treated (no test compound added) HCV infected control.
Figure 1B:
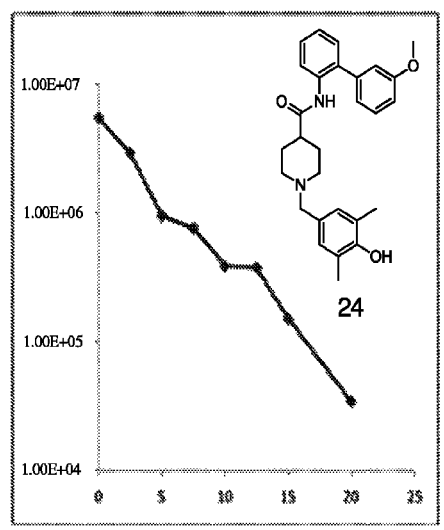
Figure 1C:
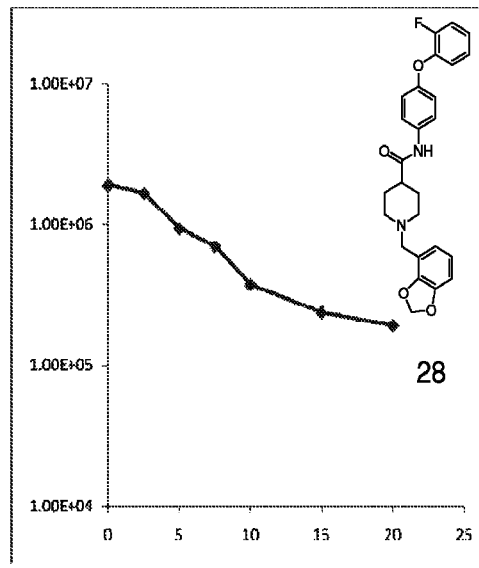

In another embodiment, pharmaceutical compositions containing one or more of the compounds are also described herein. In another embodiment, pharmaceutical compositions are in the form of a unitary dose, unit dose, or unit dosage form. In one aspect, the compositions, such as unit doses or unit dosage forms, include a therapeutically effective amount of the one or more compounds for treating a patient with a viral disease, such as HCV, BVDV, coronavirus, and/or HIV. It is to be understood that the compositions may include other components and/or ingredients, including, but not limited to, other therapeutically active compounds, and/or one or more carriers, diluents, excipients, and the like. In another embodiment, methods for using the compounds and pharmaceutical compositions for treating patients with HCV, BVDV, coronavirus, and/or HIV are also described herein. In one aspect, the methods include the step of administering one or more of the compounds and/or compositions described herein to a patient with HCV, BVDV, coronavirus, and/or HIV. In another aspect, the methods include administering a therapeutically effective amount of the one or more compounds and/or compositions described herein for treating patients with HCV, BVDV, coronavirus, and/or HIV. In another embodiment, uses of the compounds and compositions in the manufacture of a medicament for treating patients with HCV, BVDV, coronavirus, and/or HIV are also described herein. In one aspect, the medicaments include a therapeutically effective amount of the one or more compounds and/or compositions for treating a patient with HCV, BVDV, coronavirus, and/or HIV.

It is to be understood that the compounds described herein may be used alone or in combination with other compounds useful for treating HCV, BVDV, coronavirus, and/or HIV, including those compounds that may be therapeutically effective by the same or different modes of action. In addition, it is to be understood that the compounds described herein may be used in combination with other compounds that are administered to treat other symptoms of HCV, BVDV, coronavirus, and/or HIV.

In another embodiment, the methods, compositions, and unit doses and unit dosage forms described herein are illustrated by the following clauses:

1. A unit dose or unit dosage form for treating a viral infection, the unit dose or unit dosage form comprising
   (a) a therapeutically effective amount of one or more compounds of the formula

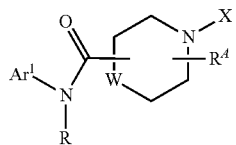

or a pharmaceutically acceptable salt thereof; wherein:
   W is carbon or nitrogen;
   $R^A$ is hydrogen or optionally substituted alkyl;
   X is alkyl, alkenyl, alkynyl, heteroalkyl, cycloalkyl, cycloalkenyl, cycloheteroalkyl, arylalkyl, heteroarylalkyl, aryl or heteroaryl, each of which is optionally substituted; or acyl;
   R is H, alkyl, heteroalkyl, acyl, alkoxycarbonyl, or aminocarbonyl, each of which is optionally substituted; or R is a prodrug moiety; and
   $Ar^1$ is aryl or heteroaryl, each of which is optionally substituted; and
   (b) one or more pharmaceutically acceptable carriers, excipients, or diluents, or combinations thereof.

2. The unit dose or unit dosage form of clause 1 comprising a therapeutically effective amount of one or more compounds of the formula

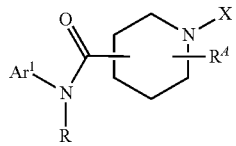

or a pharmaceutically acceptable salt thereof.

3. The unit dose or unit dosage form of clause 1 comprising a therapeutically effective amount of one or more compounds of the formula

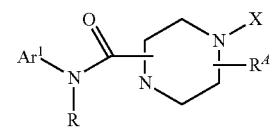

or a pharmaceutically acceptable salt thereof.

4. The unit dose or unit dosage form of any one of the preceding clauses wherein $R^A$ is H.

5. The unit dose or unit dosage form of any one of the preceding clauses wherein $R^A$ is methyl.

6. The unit dose or unit dosage form of clause 1 comprising a therapeutically effective amount of one or more compounds of the formula

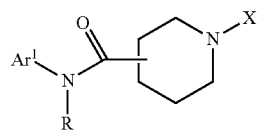

or a pharmaceutically acceptable salt thereof.

7. The unit dose or unit dosage form of clause 1 comprising a therapeutically effective amount of one or more compounds of the formula

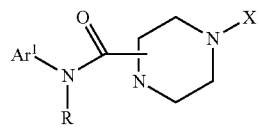

or a pharmaceutically acceptable salt thereof.

8. The unit dose or unit dosage form of any one of the preceding clauses wherein $Ar^1$ is an optionally substituted phenyl.

9. The unit dose or unit dosage form of any one of the preceding clauses wherein $Ar^1$ is phenyl substituted with optionally substituted phenyl.

10. The unit dose or unit dosage form of any one of the preceding clauses wherein $Ar^1$ is phenyl substituted with optionally substituted phenoxy.

11. The unit dose or unit dosage form of any one of the preceding clauses wherein $Ar^1$ is phenyl substituted with optionally substituted heteroaryl.

12. The unit dose or unit dosage form of any one of the preceding clauses wherein $Ar^1$ is phenyl substituted with optionally substituted benzimidazolyl.

13. The unit dose or unit dosage form of any one of the preceding clauses wherein $Ar^1$ is phenyl substituted with optionally substituted indolyl.

14. The unit dose or unit dosage form of any one of the preceding clauses wherein $Ar^1$ is arylphenyl, arylaryl, phenylphenyl, phenoxyphenyl, or 2-phenylphenyl, each of which is optionally substituted.

15. The unit dose or unit dosage form of any one of the preceding clauses wherein R is H or a prodrug moiety.

16. The unit dose or unit dosage form of any one of the preceding clauses wherein R is H.

17. The unit dose or unit dosage form of any one of the preceding clauses wherein X is optionally substituted cycloheteroalkyl.

18. The unit dose or unit dosage form of any one of the preceding clauses wherein X is optionally substituted piperidinyl.

19. The unit dose or unit dosage form of any one of the preceding clauses wherein X is an alkyl piperidinyl.

20. The unit dose or unit dosage form of any one of the preceding clauses wherein X is an N-alkyl piperidinyl.

21. The unit dose or unit dosage form of any one of the preceding clauses wherein X is acyl.

22. The unit dose or unit dosage form of any one of the preceding clauses wherein X is alkylcarbonyl, alkenylcarbonyl, or alkynylcarbonyl.

23. The unit dose or unit dosage form of any one of the preceding clauses wherein X is alkyl.

24. The unit dose or unit dosage form of any one of the preceding clauses wherein X is cycloalkyl.

25. The unit dose or unit dosage form of any one of the preceding clauses wherein X is alkenyl.

26. The unit dose or unit dosage form of any one of the preceding clauses wherein X is cycloalkenyl.

27. The unit dose or unit dosage form of any one of the preceding clauses comprising a compound of the formula

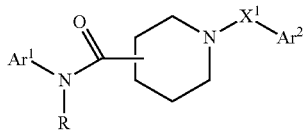

or a pharmaceutically acceptable salt thereof; wherein:
$X^1$ is a bond or $C_1$-$C_5$ alkylene, $C_1$-$C_5$ alkenylene, or C(O); and
$Ar^2$ is aryl or heteroaryl group, each of which is optionally substituted.

28. The unit dose or unit dosage form of any one of the preceding clauses wherein —C(O)NRAr$^1$ is attached at C3.

29. The unit dose or unit dosage form of any one of the preceding clauses wherein —C(O)NRAr$^1$ is attached at C4.

30. The unit dose or unit dosage form of any one of the preceding clauses comprising a compound of the formula

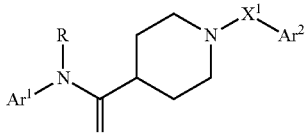

or a pharmaceutically acceptable salt thereof; wherein:
$X^1$ is a bond or $C_1$-$C_5$ alkylene, $C_1$-$C_5$ alkenylene, or C(O); and
$Ar^2$ is aryl or heteroaryl group, each of which is optionally substituted.

31. The unit dose or dosage form of any one of the preceding clauses comprising a compound of the formula

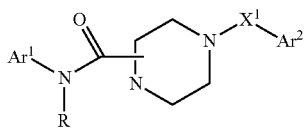

or a pharmaceutically acceptable salt thereof; wherein:
$X^1$ is a bond or $C_1$-$C_5$ alkylene, $C_1$-$C_5$ alkenylene, or C(O); and $Ar^2$ is aryl or heteroaryl group, each of which is optionally substituted.

32. The unit dose or dosage form of the preceding clause wherein —C(O)NRAr$^1$ is attached at N1.

33. The unit dose or dosage form of any one of the preceding clauses comprising a compound of the formula

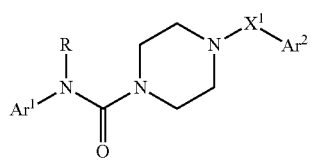

or a pharmaceutically acceptable salt thereof; wherein:
$X^1$ is a bond or $C_1$-$C_5$ alkylene, $C_1$-$C_5$ alkenylene, or C(O); and
$Ar^2$ is aryl or heteroaryl group, each of which is optionally substituted.

34. The unit dose or unit dosage form of any one of the preceding clauses wherein $X^1$ is $C_1$-$C_5$ alkylene or $C_1$-$C_5$ alkenylene.

35. The unit dose or unit dosage form of any one of the preceding clauses wherein $X^1$ is $C_1$-$C_5$ alkylene.

36. The unit dose or unit dosage form of any one of the preceding clauses wherein $X^1$ is $CH_2$.

37. The unit dose or unit dosage form of any one of the preceding clauses comprising a compound of the formula

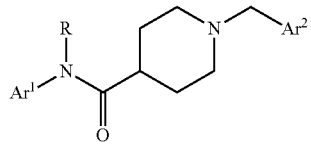

or a pharmaceutically acceptable salt thereof; wherein:
$Ar^2$ is aryl or heteroaryl group, each of which is optionally substituted.

38. The unit dose or unit dosage form of any one of the preceding clauses comprising a compound of the formula

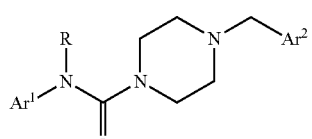

or a pharmaceutically acceptable salt thereof; wherein:
$Ar^2$ is aryl or heteroaryl group, each of which is optionally substituted.

39. The unit dose or unit dosage form of any one of the preceding clauses wherein $Ar^2$ is optionally substituted phenyl.

40. The unit dose or unit dosage form of any one of the preceding clauses wherein $Ar^2$ is substituted phenyl.

41. The unit dose or unit dosage form of any one of the preceding clauses wherein $Ar^2$ is optionally substituted heteroaryl.

42. The unit dose or unit dosage form of any one of the preceding clauses wherein $Ar^2$ is substituted heteroaryl.

43. The unit dose or unit dosage form of any one of the preceding clauses wherein $Ar^2$ is optionally substituted pyrazolyl.

44. The unit dose or unit dosage form of any one of the preceding clauses wherein $Ar^2$ is substituted pyrazolyl.

45. The unit dose or unit dosage form of any one of the preceding clauses wherein $Ar^2$ is optionally substituted furyl.

46. The unit dose or unit dosage form of any one of the preceding clauses wherein $Ar^2$ is substituted furyl.

47. The unit dose or unit dosage form of any one of the preceding clauses wherein $Ar^2$ is optionally substituted pyrazinyl.

48. The unit dose or unit dosage form of any one of the preceding clauses wherein $Ar^2$ is substituted pyrazinyl.

49. The unit dose or unit dosage form of any one of the preceding clauses wherein $Ar^2$ is optionally substituted pyridazinyl.

50. The unit dose or unit dosage form of any one of the preceding clauses wherein $Ar^2$ is substituted pyridazinyl.

51. The unit dose or unit dosage form of any one of the preceding clauses wherein $Ar^2$ is quinolinyl or methylenedioxyphenyl, each of which is optionally substituted.

52. The unit dose or unit dosage form of any one of the preceding clauses wherein $Ar^2$ is an optionally substituted quinolinyl group.

53. The unit dose or unit dosage form of any one of the preceding clauses wherein $Ar^2$ is hydroxyphenyl, methoxyphenyl, or hydroxymethoxyphenyl, each of which is optionally substituted.

54. The unit dose or unit dosage form of any one of the preceding clauses wherein the substituents are electron donating groups.

55. The unit dose or unit dosage form of any one of the preceding clauses wherein the viral infection is a DNA or RNA viral infection.

56. The unit dose or unit dosage form of any one of the preceding clauses wherein the viral infection is a HCV infection.

57. The unit dose or unit dosage form of any one of the preceding clauses wherein the viral infection is an HIV infection.

58. The unit dose or unit dosage form of any one of the preceding clauses wherein the viral infection is an BVDV infection.

59. The unit dose or unit dosage form of any one of the preceding clauses wherein the viral infection is a coronavirus infection.

60. The unit dose or unit dosage form of any one of the preceding clauses wherein the viral infection is a SARS-coronavirus infection.

61. A method for treating a viral infection in a host animal, the method comprising the step of administering to the host animal a therapeutically effective amount of one or more unit doses of any one of clauses 1 to 60.

62. The method of clause 61 wherein the viral infection is a DNA or RNA viral infection.

63. The method of clause 61 or 62 wherein the host animal is a human.

64. The method of clause 63 wherein the viral infection is a HCV infection.

65. The method of clause 63 wherein the viral infection is an HIV infection.

66. The method of clause 63 wherein the viral infection is a coronavirus infection.

67. The method of clause 63 wherein the viral infection is a SARS-coronavirus infection.

68. The method of clause 61 or 62 wherein the host animal is a bovine.

69. The method of clause 68 wherein the viral infection is a BVDV infection.

In another embodiment, various genera and subgenera of each of W, Ar1, Ar2, X, X1, and R are described herein. It is to be understood that all possible combinations of the various genera and subgenera of each of W, Ar1, Ar2, X, X1, and R described herein represent additional illustrative embodiments of compounds of the invention described herein. It is to be further understood that each of those additional illustrative embodiments of compounds may be used in any of the compositions, methods, and/or uses described herein.

In each of the foregoing and following embodiments, it is to be understood that the formulae include and represent not only all pharmaceutically acceptable salts of the compounds, but also include any and all hydrates and/or solvates of the compound formulae. It is appreciated that certain functional groups, such as the hydroxy, amino, and like groups form complexes and/or coordination compounds with water and/or various solvents, in the various physical forms of the compounds. Accordingly, the above formulae are to be understood to include and represent those various hydrates and/or solvates. In each of the foregoing and following embodiments, it is also to be understood that the formulae include and represent each possible isomer, such as stereoisomers and geometric isomers, both individually and in any and all possible mixtures. In each of the foregoing and following embodiments, it is also to be understood that the formulae include and represent any and all crystalline forms, partially crystalline forms, and non crystalline and/or amorphous forms of the compounds.

In each of the foregoing and following embodiments, derivatives are also described. Illustrative derivatives include, but are not limited to, those compounds that may be synthetically prepared from the compounds described herein, as well as those compounds that may be prepared in a similar way as those described herein, but differing in the selection of starting materials. For example, described herein are compounds that include various functional groups on aromatic rings. It is to be understood that derivatives of those compounds also include the compounds having for example different functional groups on those aromatic rings than those explicitly set forth in the definition of substituents on the compounds. In addition, it is to be understood that derivatives of those compounds also include the compounds having those same or different functional groups at different positions on the aromatic ring. Similarly, derivatives include parallel variations of other functional groups on the compounds described herein.

It is to be understood that such derivatives may include prodrugs of the compounds described herein, compounds described herein that include one or more protection or protecting groups, including compounds that are used in the preparation of other compounds described herein.

In addition, the compounds described herein may also include prodrug groups, and including the corresponding prodrugs of the various derivatives thereof. In addition, the compounds described herein may be amorphous as well as be any and all morphological forms. In addition, the compounds described herein may be in the form of solvate, including hydrates, or other solvates.

The compounds described herein may contain one or more chiral centers, or may otherwise be capable of existing as multiple stereoisomers. It is to be understood that in one embodiment, the invention described herein is not limited to any particular stereochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may be include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

As used herein, the term "alkyl" includes a chain of carbon atoms, which is optionally branched. As used herein, the terms "alkenyl" and "alkynyl" each include a chain of carbon atoms, which is optionally branched, and include at least one double bond or triple bond, respectively. It is to be understood that alkynyl may also include one or more double bonds. It is to be further understood that in certain embodiments, alkyl is advantageously of limited length, including $C_1$-$C_{24}$, $C_1$-$C_{12}$, $C_1$-$C_8$, $C_1$-$C_6$, and $C_1$-$C_4$. Illustratively, such particularly limited length alkyl groups, including $C_1$-$C_8$, $C_1$-$C_6$, and $C_1$-$C_4$ may be referred to as lower alkyl. It is to be further understood that in certain embodiments alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$. Illustratively, such particularly limited length alkenyl and/or alkynyl groups, including $C_2$-$C_8$, $C_2$-$C_6$, and $C_2$-$C_4$ may be referred to as lower alkenyl and/or alkynyl. It is appreciated herein that shorter alkyl, alkenyl, and/or alkynyl groups may add less lipophilicity to the compound and accordingly will have different pharmacokinetic behavior. In embodiments of the invention described herein, it is to be understood, in each case, that the recitation of alkyl refers to alkyl as defined herein, and optionally lower alkyl. In embodiments of the invention described herein, it is to be understood, in each case, that the recitation of alkenyl refers to alkenyl as defined herein, and optionally lower alkenyl. In embodiments of the invention described herein, it is to be understood, in each case, that the recitation of alkynyl refers to alkynyl as defined herein, and optionally lower alkynyl. Illustrative alkyl, alkenyl, and alkynyl groups are, but not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl, and the like, and the corresponding groups containing one or more double and/or triple bonds, or a combination thereof.

As used herein, the term "alkylene" includes a divalent chain of carbon atoms, which is optionally branched. As used herein, the term "alkenylene" and "alkynylene" includes a divalent chain of carbon atoms, which is optionally branched, and includes at least one double bond or triple bond, respectively. It is to be understood that alkynylene may also include one or more double bonds. It is to be further understood that in certain embodiments, alkylene is advantageously of limited length, including $C_1$-$C_{24}$, $C_1$-$C_{12}$, $C_1$-$C_8$, $C_1$-$C_6$, and $C_1$-$C_4$. Illustratively, such particularly limited length alkylene groups, including $C_1$-$C_8$, $C_1$-$C_6$, and $C_1$-$C_4$ may be referred to as lower alkylene. It is to be further understood that in certain embodiments alkenylene and/or alkynylene may each be advantageously of limited length, including $C_2$-$C_{24}$, $C_2$-$C_{12}$, $C_2$-$C_8$, $C_2$-$C_6$, and $C_2$-$C_4$. Illustratively, such particularly limited length alkenylene and/or alkynylene groups, including $C_2$-$C_8$, $C_2$-$C_6$, and $C_2$-$C_4$ may be referred to as lower alkenylene and/or alkynylene. It is appreciated herein that shorter alkylene, alkenylene, and/or alkynylene groups may add less lipophilicity to the compound and accordingly will have different pharmacokinetic behavior. In embodiments of the invention described herein, it is to be understood, in each case, that the recitation of alkylene, alkenylene, and alkynylene refers to alkylene, alkenylene, and alkynylene as defined herein, and optionally lower alkylene, alkenylene, and alkynylene. Illustrative alkyl groups are, but not limited to, methylene, ethylene, n-propylene, isopropylene, n-butylene, isobutylene, sec-butylene, pentylene, 1,2-pentylene, 1,3-pentylene, hexylene, heptylene, octylene, and the like.

As used herein, the term "cycloalkyl" includes a chain of carbon atoms, which is optionally branched, where at least a portion of the chain in cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopentyleth-2-yl, adamantyl, and the like. As used herein, the term "cycloalkenyl" includes a chain of carbon atoms, which is optionally branched, and includes at least one double bond, where at least a portion of the chain in cyclic. It is to be understood that the one or more double bonds may be in the cyclic portion of cycloalkenyl and/or the non-cyclic portion of cycloalkenyl. It is to be understood that cycloalkenylalkyl and cycloalkylalkenyl are each subsets of cycloalkenyl. It is to be understood that cycloalkyl may be polycyclic. Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including $C_3$-$C_{24}$, $C_3$-$C_{12}$, $C_3$-$C_8$, $C_3$-$C_6$, and $C_5$-$C_6$. It is appreciated herein that shorter alkyl and/or alkenyl chains forming cycloalkyl and/or cycloalkenyl, respectively, may add less lipophilicity to the compound and accordingly will have different pharmacokinetic behavior.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "aryl" includes monocyclic and polycyclic aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl, ethylaminoalkyl, dimethylaminoalkyl, methylethylaminoalkyl, and the like. Illustratively, acylamino includes acylmethylamino, acylethylamino, and the like.

As used herein, the term "amino and derivatives thereof" includes amino as described herein, and alkylamino, alkenylamino, alkynylamino, heteroalkylamino, heteroalkenylamino, heteroalkynylamino, cycloalkylamino, cycloalkenylamino, cycloheteroalkylamino, cycloheteroalkenylamino, arylamino, arylalkylamino, arylalkenylamino, arylalkynylamino, heteroarylamino, heteroarylalkylamino, heteroarylalkenylamino, heteroarylalkynylamino, acylamino, and the like, each of which is optionally substituted. The term "amino derivative" also includes urea, carbamate, and the like.

As used herein, the term "hydroxy and derivatives thereof" includes OH, and alkyloxy, alkenyloxy, alkynyloxy, heteroalkyloxy, heteroalkenyloxy, heteroalkynyloxy, cycloalkyloxy, cycloalkenyloxy, cycloheteroalkyloxy, cycloheteroalkenyloxy, aryloxy, arylalkyloxy, arylalkenyloxy, arylalkynyloxy, heteroaryloxy, heteroarylalkyloxy, heteroarylalkenyloxy, heteroarylalkynyloxy, acyloxy, and the like, each of which is optionally substituted. The term "hydroxy derivative" also includes carbamate, and the like.

As used herein, the term "thio and derivatives thereof" includes SH, and alkylthio, alkenylthio, alkynylthio, heteroalkylthio, heteroalkenylthio, heteroalkynylthio, cycloalkylthio, cycloalkenylthio, cycloheteroalkylthio, cycloheteroalkenylthio, arylthio, arylalkylthio, arylalkenylthio, arylalkynylthio, heteroarylthio, heteroarylalkylthio, heteroarylalkenylthio, heteroarylalkynylthio, acylthio, and the like, each of which is optionally substituted. The term "thio derivative" also includes thiocarbamate, and the like.

As used herein, the term "acyl" includes formyl, and alkylcarbonyl, alkenylcarbonyl, alkynylcarbonyl, heteroalkylcarbonyl, heteroalkenylcarbonyl, heteroalkynylcarbonyl, cycloalkylcarbonyl, cycloalkenylcarbonyl, cycloheteroalkylcarbonyl, cycloheteroalkenylcarbonyl, arylcarbonyl, arylalkylcarbonyl, arylalkenylcarbonyl, arylalkynylcarbonyl, heteroarylcarbonyl, heteroarylalkylcarbonyl, heteroarylalkenylcarbonyl, heteroarylalkynylcarbonyl, acylcarbonyl, and the like, each of which is optionally substituted.

As used herein, the term "carbonyl and derivatives thereof" includes the group C(O), C(S), C(NH) and substituted amino derivatives thereof.

As used herein, the term "carboxylic acid and derivatives thereof" includes the group $CO_2H$ and salts thereof, and esters and amides thereof, and CN.

As used herein, the term "sulfinic acid or a derivative thereof" includes $SO_2H$ and salts thereof, and esters and amides thereof.

As used herein, the term "sulfonic acid or a derivative thereof" includes $SO_3H$ and salts thereof, and esters and amides thereof.

As used herein, the term "sulfonyl" includes alkylsulfonyl, alkenylsulfonyl, alkynylsulfonyl, heteroalkylsulfonyl, heteroalkenylsulfonyl, heteroalkynylsulfonyl, cycloalkylsulfonyl, cycloalkenylsulfonyl, cycloheteroalkylsulfonyl, cycloheteroalkenylsulfonyl, arylsulfonyl, arylalkylsulfonyl, arylalkenylsulfonyl, arylalkynylsulfonyl, heteroarylsulfonyl, heteroarylalkylsulfonyl, heteroarylalkenylsulfonyl, heteroarylalkynylsulfonyl, acylsulfonyl, and the like, each of which is optionally substituted.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

As used herein, the terms "optionally substituted aryl" and "optionally substituted heteroaryl" include the replacement of hydrogen atoms with other functional groups on the aryl or heteroaryl that is optionally substituted. Such other functional groups illustratively include, but are not limited to, amino, hydroxy, halo, thio, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxy, thio, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

Illustrative substituents include, but are not limited to, a radical $—(CH_2)_xZ^X$, where x is an integer from 0-6 and $Z^x$ is selected from halogen, hydroxy, alkanoyloxy, including $C_1$-$C_6$ alkanoyloxy, optionally substituted aroyloxy, alkyl, including $C_1$-$C_6$ alkyl, alkoxy, including $C_1$-$C_6$ alkoxy, cycloalkyl, including $C_3$-$C_8$ cycloalkyl, cycloalkoxy, including $C_3$-$C_8$ cycloalkoxy, alkenyl, including $C_2$-$C_6$ alkenyl, alkynyl, including $C_2$-$C_6$ alkynyl, haloalkyl, including $C_1$-$C_6$ haloalkyl, haloalkoxy, including $C_1$-$C_6$ haloalkoxy, halocycloalkyl, including $C_3$-$C_8$ halocycloalkyl, halocycloalkoxy, including $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, and nitro; or $Z^x$ is selected from —$CO_2R^4$ and —$CONR^5R^6$, where $R^4$, $R^5$, and $R^6$ are each independently selected in each occurrence from hydrogen, $C_1$-$C_6$ alkyl, aryl-$C_1$-$C_6$ alkyl, and heteroaryl-$C_1$-$C_6$ alkyl.

The term "prodrug" as used herein generally refers to any compound that when administered to a biological system generates a biologically active compound as a result of one or more spontaneous chemical reaction(s), enzyme-catalyzed chemical reaction(s), and/or metabolic chemical reaction(s), or a combination thereof. In vivo, the prodrug is typically acted upon by an enzyme (such as esterases, amidases, phosphatases, and the like), simple biological chemistry, or other process in vivo to liberate or regenerate the more pharmacologically active drug. This activation may occur through the action of an endogenous host enzyme or a non-endogenous enzyme that is administered to the host preceding, following, or during administration of the prodrug. Additional details of prodrug use are described in U.S. Pat. No. 5,627,165; and Pathalk et al., Enzymic protecting group techniques in organic synthesis, Stereosel. Biocatal. 775-797 (2000). It is appreciated that the prodrug is advantageously converted to the original drug as soon as the goal, such as targeted delivery, safety, stability, and the like is achieved, followed by the subsequent rapid elimination of the released remains of the group forming the prodrug.

Prodrugs may be prepared from the compounds described herein by attaching groups that ultimately cleave in vivo to one or more functional groups present on the compound, such as —OH—, —SH, —CO$_2$H, —NR$_2$. Illustrative prodrugs include but are not limited to carboxylate esters where the group is alkyl, aryl, arylalkyl, heteroaryl, heteroarylalkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Illustrative esters, also referred to as active esters, include but are not limited to 1-indanyl, N-oxysuccinimide; acyloxyalkyl groups such as acetoxymethyl, pivaloyloxymethyl, β-acetoxyethyl, β-pivaloyloxyethyl, 1-(cyclohexylcarbonyloxy)prop-1-yl, (1-aminoethyl)carbonyloxymethyl, and the like; alkoxycarbonyloxyalkyl groups, such as ethoxycarbonyloxymethyl, α-ethoxycarbonyloxyethyl, β-ethoxycarbonyloxyethyl, and the like; dialkylaminoalkyl groups, including di-lower alkylamino alkyl groups, such as dimethylaminomethyl, dimethylaminoethyl, diethylaminomethyl, diethylaminoethyl, and the like; 2-(alkoxycarbonyl)-2-alkenyl groups such as 2-(isobutoxycarbonyl) pent-2-enyl, 2-(ethoxycarbonyl)but-2-enyl, and the like; and lactone groups such as phthalidyl, dimethoxyphthalidyl, and the like.

Further illustrative prodrugs contain a chemical moiety, such as an amide or phosphorus group functioning to increase solubility and/or stability of the compounds described herein. Further illustrative prodrugs for amino groups include, but are not limited to, ($C_3$-$C_{20}$)alkanoyl; halo-($C_3$-$C_{20}$)alkanoyl; ($C_3$-$C_{20}$)alkenoyl; ($C_4$-$C_7$)cycloalkanoyl; ($C_3$-$C_6$)-cycloalkyl($C_2$-$C_{16}$)alkanoyl; optionally substituted aroyl, such as unsubstituted aroyl or aroyl substituted by 1 to 3 substituents selected from the group consisting of halogen, cyano, trifluoromethanesulphonyloxy, ($C_1$-$C_3$)alkyl and ($C_1$-$C_3$)alkoxy, each of which is optionally further substituted with one or more of 1 to 3 halogen atoms; optionally substituted aryl($C_2$-$C_{16}$)alkanoyl and optionally substituted heteroaryl($C_2$-$C_{16}$)alkanoyl, such as the aryl or heteroaryl radical being unsubstituted or substituted by 1 to 3 substituents selected from the group consisting of halogen, ($C_1$-$C_3$)alkyl and ($C_1$-$C_3$)alkoxy, each of which is optionally further substituted with 1 to 3 halogen atoms; and optionally substituted heteroarylalkanoyl having one to three heteroatoms selected from O, S and N in the heteroaryl moiety and 2 to 10 carbon atoms in the alkanoyl moiety, such as the heteroaryl radical being unsubstituted or substituted by 1 to 3 substituents selected from the group consisting of halogen, cyano, trifluoromethanesulphonyloxy, ($C_1$-$C_3$)alkyl, and ($C_1$-$C_3$)alkoxy, each of which is optionally further substituted with 1 to 3 halogen atoms. The groups illustrated are exemplary, not exhaustive, and may be prepared by conventional processes.

It is understood that the prodrugs themselves may not possess significant biological activity, but instead undergo one or more spontaneous chemical reaction(s), enzyme-catalyzed chemical reaction(s), and/or metabolic chemical reaction(s), or a combination thereof after administration in vivo to produce the compound described herein that is biologically active or is a precursor of the biologically active compound. However, it is appreciated that in some cases, the prodrug is biologically active. It is also appreciated that prodrugs may often serves to improve drug efficacy or safety through improved oral bioavailability, pharmacodynamic half-life, and the like. Prodrugs also refer to derivatives of the compounds described herein that include groups that simply mask undesirable drug properties or improve drug delivery. For example, one or more compounds described herein may exhibit an undesirable property that is advantageously blocked or minimized may become pharmacological, pharmaceutical, or pharmacokinetic barriers in clinical drug application, such as low oral drug absorption, lack of site specificity, chemical instability, toxicity, and poor patient acceptance (bad taste, odor, pain at injection site, and the like), and others. It is appreciated herein that a prodrug, or other strategy using reversible derivatives, can be useful in the optimization of the clinical application of a drug.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

It is also appreciated that the therapeutically effective amount, whether referring to monotherapy or combination therapy, is advantageously selected with reference to any toxicity, or other undesirable side effect, that might occur during administration of one or more of the compounds described herein. Further, it is appreciated that the co-therapies described herein may allow for the administration of lower doses of compounds that show such toxicity, or other undesirable side effect, where those lower doses are below thresholds of toxicity or lower in the therapeutic window than would otherwise be administered in the absence of a cotherapy.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein. Illustratively, compositions may include one or more carriers, diluents, and/or excipients. The compounds described herein, or compositions containing them, may be formulated in a therapeutically effective amount in any conventional dosage forms appropriate for the methods described herein. The compounds described herein, or compositions containing them, including such formulations, may be administered by a wide variety of conventional routes for the methods described herein, and in a wide variety of dosage formats, utilizing known procedures (see generally, Remington: The Science and Practice of Pharmacy, ($21^{st}$ ed., 2005)).

The term "administering" as used herein includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically-acceptable carriers, adjuvants, and vehicles. It is to be understood that the unit doses and/or unit dosage forms described herein may be single or divided. It is also to be understood that the unit doses and/or unit dosage forms may be administered using a variety of daily, weekly, monthly, or quarterly dosing protocols. Examples of dosing protocols include q.d., b.i.d., t.i.d., or even every other day, once a week, twice a week, once a month, once a quarter, and the like. In each of these cases it is understood that the daily, weekly, month, or quarterly dose instance corresponds to the therapeutically effective amounts described herein. In addition, it is to be understood that when a divided dose is administered, the corresponding therapeutically effective amounts are the totals of the divided dose.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

In addition to the foregoing illustrative dosages and dosing protocols, it is to be understood that an effective amount of any one or a mixture of the compounds described herein can be readily determined by the attending diagnostician or physician by the use of known techniques and/or by observing results obtained under analogous circumstances. In determining the effective amount or dose, a number of factors are considered by the attending diagnostician or physician, including, but not limited to the species of mammal, including human, its size, age, and general health, the specific disease or disorder involved, the degree of or involvement or the severity of the disease or disorder, the response of the individual patient, the particular compound administered, the mode of administration, the bioavailability characteristics of the preparation administered, the dose regimen selected, the use of concomitant medication, and other relevant circumstances.

In making the pharmaceutical compositions of the compounds described herein, a therapeutically effective amount of one or more compounds in any of the various forms described herein may be mixed with one or more excipients, diluted by one or more excipients, or enclosed within such a carrier which can be in the form of a capsule, sachet, paper, or other container. Excipients may serve as a diluent, and can be solid, semi-solid, or liquid materials, which act as a vehicle, carrier or medium for the active ingredient. Thus, the formulation compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders. The compositions may contain anywhere from about 0.1% to about 99.9% active ingredients, depending upon the selected dose and dosage form.

The effective use of the compounds, compositions, and methods described herein for treating or ameliorating one or more effects of HCV, HIV, coronavirus, and/or BVDV using one or more compounds described herein may be based upon animal models, such as murine, canine, porcine, and non-human primate animal models of disease. For example, it is understood that HCV, coronavirus, such as SARS-CoV or MERS-CoV, and/or HIV in humans may be characterized by a loss of function, and/or the development of symptoms, each of which may be elicited in animals, such as mice, and other surrogate test animals. Further, it is understood that BVDV in bovine may be characterized by a loss of function, and/or the development of symptoms, each of which may be elicited in alternative animals, such as mice, and other surrogate test animals. Such animal models may be used to evaluate the methods of treatment and the pharmaceutical compositions described herein to determine the therapeutically effective amounts described herein.

The following examples further illustrate specific embodiments of the invention; however, the following illustrative examples should not be interpreted in any way to limit invention.

EXAMPLES

Example

Test Compounds. Illustrative substituted piperidine and piperazine carboxamides described herein are obtained from commercial suppliers (>90% purity) and used as obtained.

Other Illustrative substituted piperidine and piperazine carboxamides described herein are prepared using conventional processes.

Example

Test compound PK and tolerance in KMT Mice™. Three escalating dose levels for each of the test compounds are administered at a volume of 5 mL/kg once a day by intra-peritoneal (IP) injection. The tolerance is determined over a fourteen day treatment course. The study animals include three 5-mouse groups. Also included is one 5-mouse control group injected with 5 mL/kg of vehicle. The mouse groups include both male and female 3-month old murine KMT Mice™ with a weight range of ≥12.0 g. Blood samples are drawn via the central tail artery of the animal for measurement of serum concentrations of the test compound on the morning of Day 8 immediately prior to the drug dose (trough sample 24 hours post the Day 7 dose) and on the morning of Day 15 (trough sample 24 hours post the final Day 14 dose). A volume of approximately 100 μL is collected into tubes, allowed to clot at 2-8° C., centrifuged, and the serum removed from above the clot pellet and stored frozen at −80° C. until ready for concentration measurement.

Example

Chimeric Mouse Model. The animals used are homozygous albumin (Alb)-urokinase plasminogen activator (uPA)/severe combined immunodeficient (SCID) mice, and are housed in a virus-free/antigen-free environment until ready for use. The mouse model used herein is similar to those previously described (see, for example, N. M. Kneteman Et Al., Hepatology, 2006, 43, 1346; N. M. Kneteman Et Al., Hepatology, 2009, 49, 745).

Isolation and Transplantation of Human Hepatocytes. Segments of human liver tissue (~20 cm$^3$) are flushed with cold phosphate-buffered saline and rapidly transported to the tissue isolation laboratory. Hepatocytes are isolated and purified using collagenase-based perfusion with 0.38 mg/ml Liberase CI solution (Boehringer Mannheim), using previously described techniques (Mercer Df, Et Al., Hepatitis C Virus Replication in Mice with Chimeric Human Livers, Nat. Med. 2001, 7, 927-933). Recipient mice (5-14 days old uPA/SCID mice) are anesthetized with halothane/$O_2$, and $1 \times 10^6$ viable hepatocytes are injected into the inferior pole of the spleen. The hepatocytes then transit on their own to the liver where they implant and expand.

Human α-1 Antitrypsin Analysis. Human α-1 antitrypsin (hAAT) analysis is used to confirm stable ongoing function of the human hepatocyte grafts and to determine whether any change in HCV titer is attributable to hepatocyte death or injury. Mouse serum is analyzed by sandwich enzyme-linked immunosorbent assay as previously described (N. M. Kneteman Et Al., Hepatology, 2006, 43, 1346). Briefly, samples of mouse serum (2 μL) are diluted 1/100 in blocking buffer and analyzed by sandwich ELISA using a polyclonal goat anti-human alpha1-antitrypsin (hAAT) antibody (#81902, Diasorin, Stillwater Minn.) as the capturing antibody. A portion of the same antibody is cross-linked to horseradish peroxidase (#31489, Pierce, Rockford, Ill.) and used as the secondary antibody, with signal detection by 3,3',5,5'-tetramethylbenzidine (Sigma, St. Louis, Mo.).

HCV Isolation and Quantitation. Murine serum analysis is performed in blinded fashion using the Cobas Amplicor HCV Monitor system (Roche Diagnostics). Lower limit of quantification is 600 IU/mL. Viral RNA is extracted using Buffer AVL from Qiagen (19073) according to the manufacturer's instructions. The RNA is transcribed to cDNA with a HCV specific primer (5'-AGGTTTAGGATTCGT-GCTCAT)(SEQ ID NO: 13) with a High Capacity RNA to cDNA kit (Applied Biosystems, #4369016) according to the manufacturer's directions. RT-PCR is performed using an ABI 7300 Real Time PCR system and Taqman chemistry, with all measurements done in duplicate. 6-FAM-CAC-CCTATCAGGCAGTACCACAAGGCC-TAMRA (SEQ ID NO: 14) is used as the HCV specific detection probe and a primer set detecting the conserved 5'UTR region of HCV (5'-TGCGGAACCGGTGAGTACA (SEQ ID NO: 15), 5'-AGGTTTAGGATTCGTGCTCAT (SEQ ID NO: 13)). For absolute quantitation, a standard curve of known dilutions of a plasmid containing the sequence for HCV variant H77c (pCV-H77c) is created, alongside an Optiquant HCV RNA high control (Optiquant).

Experimental Conduct. Six weeks after hepatocyte transplantation, mice are screened for serum hAAT, and animals above a 100 μg/mL cutoff are inoculated by intraperitoneal injection with 100 μg genotype 1a HCV-laden human serum (approximately $2 \times 10^5$ copies/mL). Baseline HCV levels are obtained at 1 and 2 weeks after inoculation, and mice with titers above $2 \times 10^4$ copies/mL are allocated to experimental groups. Allocation sought to balance groups for HCV titers, hAAT levels, sex, and weight with decreasing priority.

Example

Efficacy against HCV infection in KMT Mice™. The protocol includes three dose levels that are selected based on the tolerability and PK results from the study described in the previous Example. The efficacy of each test compound is determined over a fourteen day treatment course and seven day follow-up period employing three escalating dose levels of test compound administered at a volume of 5 mL/kg once a day by intraperitoneal injection. The baseline animal acceptance criteria are as follows—minimum hAAT value=80; minimum HCV value=$1 \times 10^4$ IU/mL; health status cutoff ≤1-2. The study animals include three 5-mouse groups. Also included is one 5-mouse control group injected with 5 mL/kg of vehicle. The mouse groups include both male and female 3-month old murine KMT Mice™ with a weight range of ≥12.0 g. Blood samples are drawn via the central tail artery for measurement of baseline serum concentrations of hAAT and HCV on Day 3. Subsequent blood draws are made the morning of Day 7, immediately prior to test compound dosing, the morning of Day 14, twenty-four hours after the final test compound dose administered at approximately 0800 h the previous day and on Day 21, seven days after the last test compound dose. A volume of approximately 100 μL is collected into tubes, allowed to clot at 2-8° C., centrifuged and the serum removed from above the clot pellet. Serum samples are stored frozen at −80° C. until ready for testing for HCV and hAAT levels.

Example

In vitro assay for anti-HCV efficacy. HCV studies typically involve infected patients and chimpanzees. However, recently, a robust HCV infection system was developed with cells derived from the Huh-7 human hepatoma cell line. It is based on the unique JFH-1 HCV consensus cDNA derived from an HCV patient. Using reverse genetics, the infectious virus can be rescued from this HCV clone. The recovered viable JFH virus can be passaged serially in Huh-7 cells. For this reason, this system is amenable for evaluating the activity of test compound for their anti-HCV efficacy.

Briefly, 6×10³ Huh7-1 cells are incubated overnight in each well of collagen-coated BioCoat 96-well plates (BD Biosciences, Bedford, Mass.) in 0.2 ml 10% medium composed of Dulbecco's modified Eagle's medium supplemented with 10% fetal bovine serum. Subsequently, at 2 day intervals, the cultures are replenished with fresh 0.2 ml 10% medium. After the cultures become confluent, they continue to be replenished at 2 day intervals with fresh 0.2 ml 10% medium that also includes 1% dimethyl sulfoxide (DMSO). After 20 days of these replenishments, the Huh7-1 cultures are incubated with fresh 1% medium (same as 10% medium except that the serum level is 1%) containing HCV at a multiplicity of infection (MOI) of 0.05 focus forming units (ffu)/cell. The HCV (JFH-1wt Huh7) stock titer is 1.5×10⁵ ffu/mL. The next day (day 1 post-infection) and 2 days later (day 3 post-infection) the media are replenished with fresh 1% medium containing the test compounds dissolved in DMSO. On the 5th day of treatment with the compounds, cell lysates are collected for RNA isolation and Real Time-quantitative Reverse Transcription Polymerase Chain Reaction (RT-qPCR) and culture media are collected for cytotoxicity analysis.

Total RNA is isolated from cells by the guanidine thiocyanate method using standard protocols. One µg RNA is used for cDNA synthesis using TaqMan reverse transcription reagents (Applied Biosystems, Foster City, Calif.) followed by real-time PCR using an Applied Biosystems 7300 real-time thermocycler. Thermal cycling consists of initial denaturation of 10 min at 95° C. followed by 40 cycles of denaturation (15 s at 95° C.) and annealing/extension (1 m at 60° C.). HCV and human glyceraldehyde-3-phosphate dehydrogenase (GAPDH) RNA levels are determined relative to a standard curve of serial dilutions of plasmid containing JFH-1 HCV or GAPDH cDNA. The PCR primers used to detect GAPDH and HCV are: GAPDH (NMX002046) 5'-GAAGGTGAAGGTCGGAGTC-3'(SEQ ID NO: 16) (sense) and 5'-GAAGATGGT-GATGGGATTTC-3'(SEQ ID NO: 17) (anti-sense) JFH-1 HCV (AB047639) 5'-TCTGCGGAACCGGTGAGTA-3' (SEQ ID NO: 18) (sense) and 5'-TCAGGCAGTACCA-CAAGGC-3'(SEQ ID NO: 19) (anti-sense).

Example

The compounds and antiviral activities in the following table are described herein. In each of the compounds described herein, it is to be understood that each atom includes a full valence, where each remaining atom is hydrogen.

Illustrative compounds and antiviral activity. All Example compounds tested at multiple doses show a dose response.

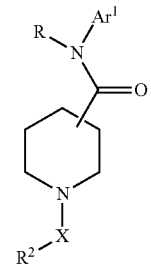

| Example | Ar¹ | R | Ring Connection | X | R² | HCV Antiviral Activity |
|---|---|---|---|---|---|---|
| 16 | 3-(3-FC₆H₄)C₆H₄ | H | C4 | CH₂ | Quinolin-8-yl | ++ |
| 17 | 4-(3-MeC₆H₄)C₆H₄ | H | C4 | CH₂ | 4-OH-3-MeO—C₆H₃ | + |
| 19 | 3-(3-MeC₆H₄)C₆H₄ | H | C3 | (CH₂)₃ | 1-pyrazolyl | NT |
| 20 | 3-(3-MeC₆H₄)C₆H₄ | H | C3 | CH₂ | 1-(2-Pyrimidinyl)pyrrol-2-yl | NT |
| 21 | 4-(2-FC₆H₄O)C₆H₄ | H | C4 | CH₂ | 2-OH-4-MeO—C₆H₃ | +++ |
| 22 | 2-(3-MeOC₆H₄)C₆H₄ | H | C4 | CH₂ | Quinolin-8-yl | +++ |
| 23 | 4-(Benzimidazol-2-yl)C₆H₄ | H | C4 | CH₂ | 2-MeO—C₆H₄ | +++ |
| 24 | 2-(3-MeOC₆H₄)C₆H₄ | H | C4 | CH₂ | 4-OH-3,5-Me₂—C₆H2 | +++ |
| 25 | 2-(3-MeOC₆H₄)C₆H₄ | H | C4 | CH₂ | 2-MeO—C₆H₄ | ++ |
| 26 | 3-(3-FC₆H₄)C₆H₄ | H | C4 | CH₂ | 4-OH—C₆H₄ | ++ |
| 27 | 3-(3-FC₆H₄)C₆H₄ | H | C4 | CH₂ | 2-(n-Bu)-imidazol-4-yl | ++ |
| 28 | 4-(2-FC₆H₄O)C₆H₄ | H | C4 | CH₂ | 2,3-Methylenedioxy-C₆H₃ | ++ |
| 29 | 3-(3-FC₆H₄)C₆H₄ | H | C4 | CH₂ | 3-OH—C₆H₄ | + |
| 30 | 3-(3-FC₆H₄)C₆H₄ | H | C4 | CH₂ | 2-OH-6-MeO—C₆H₃ | + |
| 31 | 3-(3-ClC₆H₄)C₆H₄ | H | C4 | CH₂ | 4-OH—C₆H₄ | + |
| 32 | 2-(3-MeOC₆H₄)C₆H₄ | H | C4 | CH₂ | 3-Me-4-MeO—C₆H₃ | + |
| 33 | 2-(3-MeOC₆H₄)C₆H₄ | H | C4 | CH₂ | 3-MeO—C₆H₄ | + |
| 34 | 2-(3-MeOC₆H₄)C₆H₄ | H | C4 | CH₂ | 4-F-2-MeO—C₆H₃ | + |
| 35 | 3-(4-Thiazolyl)C₆H₄ | H | C4 | CH₂ | 3-(2-Furyl)C₆H₄ | + |
| 36 | 2-(3-MeOC₆H₄)C₆H₄ | H | C4 | CH₂CH₂CH(Me) | Ph | + |
| 38 | 3-(2-Indolyl)C₆H₄ | H | C4 | CH₂ | (1-i-Pr-pyrazol-4-yl) | + |
| 39 | 2-(3-MeOC₆H₄)C₆H₄ | H | C4 | CH₂ | t-Bu | + |
| 40 | 3-(2-Furyl)C₆H₄ | H | C4 | CH₂ | Quinolin-8-yl | + |
| 41 | 3-(2-Me-1,3,4-thiazol-5-yl)C₆H₄ | H | C4 | C(=O) | 2-Furyl | + |
| 42 | 3-(3-ClC₆H₄)C₆H₄ | H | C4 | CH₂ | 4-OH-3-MeO—C₆H₃ | + |
| 43 | 3-(5-Pyrazolyl)C₆H₄ | H | C4 | CH₂ | 1-Naphthyl | − |
| 45 | 3-(2-Indolyl)C₆H₄ | H | C4 | CH₂ | (5-Me)-2-furyl | − |
| 46 | 3-(2-Indolyl)C₆H₄ | H | C4 | CH₂CH₂CH₂ | SMe | − |
| 47 | 4-(Benzimidazol-2-yl)C₆H₄ | H | C4 | CH₂ | 2-Indolyl | − |
| 48 | 2-(3-MeOC₆H₄)C₆H₄ | H | C4 | CH₂ | 4-EtO—C₆H₄ | − |
| 49 | 3-(2-Furyl)C₆H₄ | H | C4 | CH₂ | 6-F-Benzimidazol-2-yl | − |
| 50 | 3-(3-ClC₆H₄)C₆H₄ | H | C4 | CH₂ | 3-OH—C₆H₄ | − |
| 51 | 3-(2-Furyl)C₆H₄ | H | C4 | C(=O) | 3-Furyl | − |
| 52 | 3-(4-Thiazolyl)C₆H₄ | H | C4 | CH₂CH=CH(E) | 4-F—C₆H₄ | − |

-continued

| Example | Ar¹ | R | Ring Connection | X | R² | HCV Antiviral Activity |
|---|---|---|---|---|---|---|
| 53 | 3-(2-Furyl)C₆H₄ | H | C4 | C(=O)CH₂CH₂ | 2-Furyl | − |
| 54 | 3-(2-Furyl)C₆H₄ | H | C4 | C(=O) | 4,5-Trimethylenepyrazol-3-yl | − |
| 55 | 3-(2-Furyl)C₆H₄ | H | C4 | CH₂CH=CH(E) | 4-MeO—C₆H₄ | − |
| 56 | 3-(3-FC₆H₄)C₆H₄ | H | C4 | CH₂ | 2,3-Methylenedioxy-C₆H₃ | − |
| 57 | 3-indol-2-ylC₆H₄ | H | C4 | C(O) | C≡C—CH₃ | ++ |
| 58 (427) | 4-benzimidazol-2-ylC₆H₄ | H | C4 | CH₂ | 3-MeO—C₆H₄ | ++ |
| 59 (252) | 4-benzimidazol-2-ylC₆H₄ | H | C4 | CH₂ | 5-Et-furan-2-yl | ++ |
| 60 (308) | 3-indol-2-ylC₆H₄ | H | C4 | C(O) | thiazol-5-yl | + |
| 61 (P101) | 4-(2-FC₆H₄O)C₆H₄ | H | C4 | CH₂ | 2-HO-3-MeO—C₆H₃ | ++ |
| 62 (P102) | 2-(3-MeOC₆H₄)C₆H₄ | H | C4 | CH₂ | 2-HO-3-MeO—C₆H₃ | ++ |
| 63 (P104) | 3-(3-ClC₆H₄)C₆H₄ | H | C4 | CH₂ | 2-HO-3-MeO—C₆H₃ | ++ |
| 64 (P106) | 4-(2-FC₆H₄O)C₆H₄ | H | C4 | CH₂ | Et | ++ |
| 65 (P107) | 4-benzimidazol-2-ylC₆H₄ | H | C4 | CH₂ | 3-MeO—C₆H₄ | ++ |
| 66 | 4-(3,5-Me₂-pyrazol-1-yl) C₆H₄ | H | C4 | CH₂CH=CH(E) | 2-MeO—C₆H₄ | + |
| 68 | 3-(3-FC₆H₄)C₆H₄ | H | C4 | CH₂ | 2-Et-5-Me-imidazol-4-yl | + |
| 69 | 3-(3-MeOC₆H₄)C₆H₄ | H | C4 | CH₂ | CH=C(Me)₂ | ++ |
| 70 | 4-(2-FC₆H₄O)C₆H₄ | H | C4 | CH₂ | 3-MeO—C₆H₄ | + |
| 71 | 2-(3-MeOC₆H₄)C₆H₄ | H | C4 | CH₂ | naphtha-1-yl | + |
| 72 | 3-(3-ClC₆H₄)C₆H₄ | H | C4 | CH₂ | 1-allyl-3-Me-pyrazol-4-yl | + |
| 73 | 4-(2-FC₆H₄O)C₆H₄ | H | C4 | CH₂ | 1-Pr-5-Me-pyrazol-4-yl | + |
| 74 | 4-(2-FC₆H₄O)C₆H₄ | H | C4 | CH₂ | Me | ++ |
| 75 | 4-(2-FC₆H₄O)C₆H₄ | H | C4 | - | 1-Et-piperidin-4-yl | +++ |
| 76 | 3-(3-FC₆H₄)C₆H₄ | H | C4 | CH₂ | 1-(i-Pr)-3,5-Me2-pyrazol-4-yl | ++ |
| 77 | 2-PhO-pyridin-5-yl | H | C4 | CH₂ | Ph | ++ |
| 78 | 3-(3-ClC₆H₄)C₆H₄ | H | C4 | CH₂ | 1-Et-pyrazol-4-yl | ++ |
| 79 | 3-(3-FC₆H₄)C₆H₄ | H | C4 | CH₂ | 3,5,6-Me₃-pyrazin-2-yl | ++ |
| 80 | 2-(3-MeOC₆H₄)C₆H₄ | H | C4 | CH₂ | 1-Pr-5-Me-pyrazol-4-yl | + |
| 81 | 4-(2-FC₆H₄O)C₆H₄ | H | C4 | CH₂ | 2-HO-5-MeO—C₆H₃ | ++ |
| 82 | 3-(3-ClC₆H₄)C₆H₄ | H | C4 | CH₂ | 1-(i-Pr)-pyrazol-4-yl | + |
| 83 | 2-PhO-pyridin-5-yl | H | C4 | CH₂ | 5-Cl-thien-2-yl | ++ |
| 84 | 3-(3-FC₆H₄)C₆H₄ | H | C4 | CH₂ | 2,3-(MeO)₂—C₆H₃ | + |
| 85 | 4-(2-FC₆H₄O)C₆H₄ | H | C4 | CH₂ | 4-HO-3-MeO—C₆H₄ | ++ |
| 86 | 4-(2-FC₆H₄O)C₆H₄ | H | C4 | CH₂ | 5-(i-Bu)-pyrazol-3-yl | + |
| 87 | 2-(3-MeOC₆H₄)C₆H₄ | H | C4 | CH₂ | 3,5,6-Me₃-pyrazin-2-yl | ++ |
| 88 | 2-(3-MeOC₆H₄)C₆H₄ | H | C4 | CH₂ | 2,5-Me₂—C₆H₃ | + |
| 90 | 3-(3-FC₆H₄)C₆H₄ | H | C4 | CH₂ | Benzo-2,1,3-thiadiazol-5-yl | + |
| 91 | 3-(3-FC₆H₄)C₆H₄ | H | C4 | CH₂ | 2-HO-3-MeO—C₆H₃ | ++ |
| 92 | 4-(benzimidazol-2-yl)C₆H₄ | H | C4 | CH₂ | Cyclohexen-4-yl | + |
| 93 | 3-(3-FC₆H₄)C₆H₄ | H | C4 | CH₂ | 1-allyl-3-Me-pyrazol-4-yl | ++ |
| 94 | 4-(2-FC₆H₄O)C₆H₄ | H | C4 | CH₂ | 5-Me-furan-2-yl | + |
| 95 | 3-(3-FC₆H₄)C₆H₄ | H | C4 | CH₂ | 1-Et-5-Me-pyrazol-4-yl | ++ |
| 96 | 4-(benzimidazol-2-yl)C₆H₄ | H | C4 | CH₂ | 3-FC₆H₄ | + |
| 97 | 4-(2-FC₆H₄O)C₆H₄ | H | C4 | CH₂ | 1-Et-pyrazol-4-yl | ++ |
| 98 | 3-(3-ClC₆H₄)C₆H₄ | H | C4 | CH₂ | Pyridin-2-yl | + |

Antiviral Activity: Cell survival compared to untreated control.
"+++" corresponds to ≤30% viral titer at 5 μM
"++" corresponds to ≤60% viral titer at 5 μM
"+" corresponds to ≤60% viral titer at 15 μM
"−" corresponds to >60% viral titer at 15 μM (highest concentration tested)
"NT" = not tested

Example

HCV Induced Cytotoxicity Test. Test compounds are evaluated for cytotoxicity at doses used for efficacy using the Promega CytoTox 96 Non-Radioactive Cytotoxicity Assay kit (Promega, Madison, Wis.). This kit measures lactate dehydrogenase (LDH) levels in the culture medium, which is released from cells due to plasma membrane integrity loss or necrosis. For this test, 50 μL samples of culture medium are collected from the same 5 day cultures used to examine the RNA levels shown previously. Test compounds described herein are not generally cytotoxic at the tested doses, and do not generally cause apparent Huh?-1 cell damage.

At doses greater than 5 μM, compounds described herein are as effective as 100 U/mL IFN-β-1b, 10 and 80 μM RBV, and 10 and 15 μM MA in reducing HCV-mediated cellular damage, as observed in the Mock-treated, HCV-infected untreated control samples.

Example

Co-therapy Treatment for HCV Infection. Effective treatment of HCV infected patients has been reported to require both RBV and IFN-β-1b because that combination is more potent than each drug on its own. The compounds described herein are tested to determine whether they increase the efficacy of either RBV, IFN-β-1b, or a combination thereof. Using the protocol described for determining chemical-evoked reduction in intracellular HCV RNA, the cells are treated with and without 10 U/mL IFN-β-1b in combination with 2.5 or 10 µM of the compounds described herein and for comparison with 10 µM MA and 80 µM RBV.

The results, shown in Table 1, indicate that these combinations are more effective than the individual treatments. The most active treatment is INF-β-1b plus MA, followed in decreasing order by IFN-β-1b plus compound 16, then IFN-β-1b plus RBV. It is observed that the combination of IFN-β-1b with compound 16 is more effective than that achieved with RBV even though RBV is used at almost an order of magnitude higher dose than compound 16.

Taken together, the results in the following table indicate that the combination of compound 16 with IFN-β-1b reduces intracellular HCV RNA levels more effectively than either agent alone.

| Example | Average HCV copies/µg RNA | Fold Inhibition |
|---|---|---|
| Untreated Control | $9.3 \times 10^6$ | 1 |
| IFN-β-1b | $1.9 \times 10^5$ | 48 |
| 16 (2.5 µM) | $3.3 \times 10^6$ | 3 |
| +IFN-β-1b | $1.1 \times 10^5$ | 85 |
| 16 (10 µM) | $2.0 \times 10^6$ | 5 |
| +IFN-β-1b | $9.6 \times 10^4$ | 97 |
| MA (10 µM) | $1.7 \times 10^6$ | 5 |
| +IFN-β-1b | $4.4 \times 10^4$ | 211 |
| RBV (80 µM) | $5.0 \times 10^6$ | 2 |
| +IFN-β-1b | $1.8 \times 10^5$ | 52 |

Example

Assay against HIV replication in PBMCs. 10 mL BD Vaccutainer, heparin coated (#367874) tubes are used to collect blood from healthy donors after consent. Average of $10 \times 10^6$ PBMCs per 10 mL tube of blood is used to determine total amount of blood drawn from each donor. Test compounds are evaluated using conventional assays for the viability of IL-2 and phytohaemagglutinin (PHA)-stimulated cultured human peripheral blood mononuclear cells (PBMC) in the presence of test compounds. Test compounds are evaluated using conventional assays on HIV replication in such cells infected with HIV. Control Cell viability is determined by a colormetric assay, such as MTS (Promega catalogue #G3582) and HIV replication by measuring the level of HIV capsid p24 antigen (5) using an ELISA kit supplied by the NIH. The substituted piperidine and piperazine carboxamides are dissolved in dimethyl sulfoxide (DMSO) and used at a final concentration of 25 µM. The final DMSO concentration in the growth medium is 0.5%. Azidothymidine (AZT), at a final concentration of 1 µM, serves as a positive control while DMSO in the absence of the piperidine and piperazine carboxamides or AZT serves as a negative control.

Example

Isolation and stimulation of peripheral blood mononuclear cells (PBMCs). For the cell viability assay and P24 level assessment after piperidine and piperazine carboxamide treatment, freshly isolated blood is collected from healthy consented donors using a 10 mL heparin coated tube (BD Vaccutainer #367874). The collected blood containing about $10^7$ PBMC is dilute by mixing with an equal amount of sterile phosphate buffered saline (PBS) in 50 mL tube. The blood/PBS mixture (e.g. 40 mL) is then slowly overlaid onto 10 mL lymphocyte separation medium (Lonza, Walkersville, Md.) and centrifuged at 2000 rpm for 15 min at room temperature in a Beckman Gs-6R centrifuge with break off. The PBMC are removed from the 50 mL centrifuge tube by aspiration using a sterile Pasteur pipette and placed into a 15 mL centrifuge tube to which PBS is added to fill the tube. To remove platelets, the tube is centrifuged at 2000 rpm for 5 mM (with the break on) in order to pellet the freshly isolated PBMC. The buffy coat containing PBMCs is carefully removed and washed 3 times with PBS at 1400 rpm to remove residual platelets. The supernatant with the platelets is decanted and PBS added to the tube to a 15 mL volume and centrifuged at 1400 rpm for 5 mM after which time the supernatant is decanted and the pellet suspended in 5 mL growth medium (RPMI-1640 medium plus 10% fetal bovine serum, 1% 1-glutamine and 1% penicillin/streptomycin) with 20 units/ml IL-2 and 4 µg/ml PHA and incubated for a day in T25 culture flasks at 37° C. and 5% $CO_2$ in a humidified incubator. For stimulation, 4 µg/mL of PHA and 20 units/mL of IL-2 are added to the cells and incubated in a T25 flask for 24 h at 37° C. in a 5% $CO_2$ humidified incubator. All steps are performed in sterile conditions.

Example

Infection of PBMCs with HIV-1 Bal: HIV-1 Bal (NIH AIDS Research and Reference Reagent Program, Frederick, Md.) at a concentration of 2 ng virus/$10^6$ cells was added to stimulated PBMCs and incubated for 5 h at 37° C., in a 5% $CO_2$, humidified incubator. Cells were then washed with media three times.

Example

HIVp24 assay. p24 is a component of the HIV capsid and its detection is used to indicate the presence of the virus. For p24 assays, $10^6$ cells per condition were resuspended in 1 mL of RPMI complete medium with 20 units/mL IL-2. Cells are left untreated or treated with 1.25 mM azidodeoxythymidine (AZT), an HIV reverse-transcriptase inhibitor (Sigma, St Louis, Mo.), as a positive control or 1.25 mM dimethyl sulfoxide (DMSO), as the vehicle control, or the test compounds at the different concentrations. For p24 assays, the infected and treated cells were then plated in a 96 well U-bottom plate at 200,000 cells in 200 µL volume of the media in quadruplicates for 6 days at 37° C., in a 5% $CO_2$, humidified incubator.

Supernatants are harvested 6 days after infection and lysed with p24 lysis buffer (10% triton-X100 in Milli-Q water) at 1:10 ratio in a 96 well culture plate. The plate is then incubated at 37° C. for 1 h in order to lyse the virions. The p24 ELISA kits may be obtained from SAIC-Frederick (Frederick, Md.) and the assay is performed according to the manufacturer's protocol. Briefly, the test plate is washed three times with 200 µL of wash buffer, and 100 µL of serially diluted standards (stock provided) or sample was added to the wells and incubated for 2 h at 37° C. The plate is then washed three times with 200 µL of wash buffer and 100 µL of primary antibody solution (at manufacturer's recommendation specific for kit used) is added to each well and the plate is again incubated for 1 h at 37° C. The plate is again washed three times and 100 µL of secondary antibody solution (at manufacturer's recommendation specific for kit used) is added to each well followed by incubation for 1 h at 37° C. The plate is washed for final three times and 100 µL of TMB solution (KPL, Gaithersburg, Md.) is added to each well and incubated for 30 min at RT in dark. The reaction is stopped with 100 µL 1N NaCl and the plate is read on a plate reader at 450 nm with a 650 nm background. A four parameter analysis is used to calculate the standard curve and concentration based on absorbance readings.

For RNA isolation and subsequent real time PCR studies, $3 \times 10^6$ infected and washed cells were resuspended in RPMI complete medium with 20 units/mL of IL-2 and subjected to appropriate treatments as mentioned above and cultured at 1 mL volume in 12 well culture plates for 1 to 3 days (depending on testing time points of HIV replication cycle) at 37° C., 5% $CO_2$ humidified incubator.

Example

HIV replication inhibition is determined by assaying the effect of test compounds on the levels of the HIV capsid protein p24 (6) in HIV-infected PBMC. The amount of P24 is assayed by using a sandwich ELISA assay kit obtained from SAIC-Frederick AIDS (Frederick, Md.) reagent program and performed according to the manufacturer's protocol. The kit includes a coated plate, standards, primary and secondary antibodies. For this P24 determination, a day after stimulation of the PBMC with IL-2 and PHA, samples of the stimulated PBMC containing about $10^6$ cells are centrifuged for 5 min at 2000 rpm. The supernatant is decanted and 2 ng of HIV-Bal virus stock provided by the NIH AIDS Reagent and Reference Program is added to each pellet and the cells suspended with growth medium to a total of 1 mL and incubated at 37° C. and 5% $CO_2$ in a humidified incubator. After 4 h, the cells are washed 3 times with 5 mL growth medium at 2000 rpm for 5 min. The final pellet is resuspended in fresh growth medium to which 20 units/mL IL-2 is added. Aliquots of 1 mL PBMC suspension containing around $10^6$ cells per mL are placed into 1.5 mL microcentrifuge tubes and treated with the test chemicals. For each treatment, 4 aliquots of 200 µL (about $2 \times 10^5$ cells) are each dispensed into separate wells of a U-bottom 96 well plate and incubated at 37° C. and 5% $CO_2$ in a humidified incubator.

After 7 day incubation, the supernatant from each well is transferred to a flat bottom 96 well plate and lysed with a ⅒ volume of 10% Triton-x 100 in DI-H2O at 37° C. for 1 h. The test plates are washed three times with 200 µL of wash buffer. 100 µL of standards at 40 ng/mL, 20 ng/mL, 10 ng/mL, 5 ng/mL, 2.5 ng/mL, 1.25 ng/mL, 0.625 ng/mL, 0.3125 ng/mL, 0.1563 ng/mL and 0 ng/mL of p24 lysate control as well as 100 µL of test samples diluted 1:10 in 1% BSA, 0.2% Tween 20 in RPMI are added into the antigen-coated 96 well plate. The plates are incubated at 37° C. for 2 h and washed three times with 200 µL wash buffer. 100 µL of primary antibody solution diluted 1:150 in 10% fetal bovine serum, 2% normal mouse serum in RPMI medium is added to each well and the plates are incubated at 37° C. for 1 h. After three washes with 200 µL wash buffer, 100 µL of secondary antibody diluted 1:50 in 2% normal mouse serum, 5% NGS, 0.01% Tween 20 in RPMI medium is added. The plates are incubated at 37° C. for 1 h and washed three times with 200 µL wash buffer. 100 µL of TMB, prepared by mixing equal volumes of each component solution provided with the KPL kit (KPL, Gaithersburg, Md.), are added to each well and the plate is incubated at room temperature, in the dark for 30 min. The reaction is stopped by adding 100 µL 1N NaCl and the plates are read using a plate reader at 450 nm with a 650 nm background. A four parameter analysis is used to calculate the standard curve and concentration based on absorbance readings.

Example

PBMCs are infected for five hours and washed three times with media. PBMCs are then treated with test compound, illustratively at 2 µM, 10 µM, and 25 µM. HIV p24 is measured 7 days post-infection. Test compounds are test for inhibition of HIV p24. PBMCs are treated with test compounds, illustratively at 2 µM, 10 µM, and 25 µM for three days. MTS assay are performed post 3 days of treatment, and readings are taken at 490 nm. Cells are evaluated for viability in the presence of test compounds.

Example

Cell viability is assayed by the "CellTiter 96® AQueous One Solution Cell Proliferation Assay" (Promega, #G3582), which assesses the metabolic activity of cells by measuring their ability to reduce MTS (3-(4,5-dimethylthiazol-2-yl)-5-(3-carboxymethoxyphenyl)-2-(4-sulfophenyl)-2H-tetrazolium in the presence of phenazine methosulfate into a formazan product that has an absorbance maximum at 490-500 nm (4). For this assay, $10^6$ stimulated PBMC in 1 mL of growth medium are each aliquoted into 1.5 mL microcentrifuge tubes and treated with the substituted piperidine and piperazine carboxamides at a final concentration of 25 µM. The control is only treated with a final concentration of 0.5% DMSO, which is the test compound solvent. After treatment, $10^5$ PBMC in 100 µL growth medium are each inoculated into a well of a 96 well flat bottom plate with 4 replicates for the control and each of the substituted piperidine and piperazine carboxamides. After 6 days of incubation of the plate at 37° C. with 5% $CO_2$ in a humidified incubator treatment, 20 µL of MTS solution (Promega, #G3582) is added to each well and the plate incubated for 4 hrs at 37° C. with 5% $CO_2$ in a humidified incubator, at which time the developing color is read at an absorbance of 490 nm on a plate reader.

Example

HIV entry. For HIV entry analysis, stimulated PBMCs are pre-treated with test compounds at desired concentrations and AZT (control) for 1 h and 4 h. The PBMCs are then infected with HIV-Bal (2 ng/mL per $10^6$ cells) for 5 h. The cells are then washed with media and treated with trypsin to remove bound virus. The cells are washed two more times and RNA from samples is isolated using RNEasy MiniKit (Qiagen). DNA contamination is removed by DNaseI (Sigma) treatment at RT for 15 min followed by denaturation of DnaseI at 70° C. for 10 min cDNA synthesis is performed using qScript cDNA supermix. Using this cDNA, real time RT-PCR is performed to quantify target genes of interest. The following primers are used to amplify HIV transcripts: HIV LTR, Forward 5'-TCAAGTGAGTGCCCGGTT (SEQ ID NO: 1) and Reverse 5'-AGCTCCG-GTTTCTCTTTCGCT (SEQ ID NO: 2) and GAPDH—Forward 5'-TGACTTCAACAGCGACACCCACT (SEQ ID NO: 3) and Reverse 5'-ACCACCCTGTTGCTGTAGC- CAAAT (SEQ ID NO: 4). GADPH is used as endogenous control. Example 57 did not have an effect on HIV entry at 10 μM or 25 μM.

Example

Figure 2:
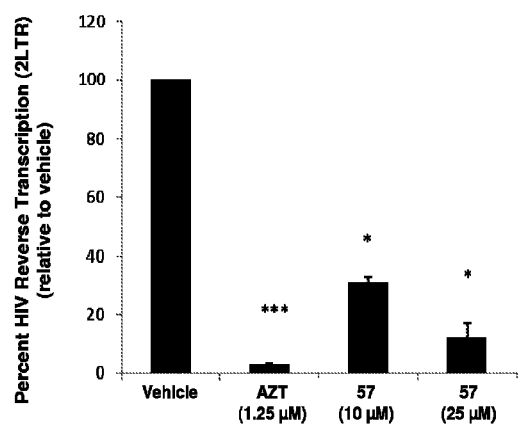
FIG. 2 shows that Example 57 significantly inhibits HIV reverse transcription.

HIV reverse transcription assay. Compounds described herein inhibit 2LTR circles. Stimulated PBMCs are infected with HIV-Bal (2 ng/mL per $10^6$ cells) for 5 h. PBMCs are then treated with compounds at desired concentrations and AZT (control) for 72 h post-infection. The cells are then washed three times with media and genomic DNA is prepared from samples using DNeasy Blood and Tissue Kit (Qiagen). For real time PCR analysis, the following primers are used to amplify 2LTR circles (by-products of reverse transcription): Forward 5'-AACTAGGGAACCCACTGCT-TAAG (SEQ ID NO: 5) and Reverse 5'-CCCACAAAT-CAAGGATATCTTGTC (SEQ ID NO: 6). AZT (1.25 μM, a reverse transcriptase inhibitor as positive control) significantly inhibits HIV reverse transcription. FIGS. 2 and 4 show that compounds described herein significantly inhibit reverse transcription at each concentration and appears to start to inhibit at the reverse transcription level. All results represent two or three independent experiments each performed in quadruplicates; *=$p<0.05$, =$p<0.01$, *=$p<0.001$ in comparison with vehicle (1.25 μM DMSO).

Without being bound by theory, it is believed herein that the unevenness of some of the HIV results may be due to the variability in the responses of normal human PBMC from different individuals. Total donors (n)=3. The data indicate that the compounds described herein are useful in treating HIV infection. In addition, the data show that the compounds are not generally cytotoxic. Though the data show a trend to lower cell viability, the differences between the control and each of the test doses were not statistically significant in the cytotoxicity assay. Thus, without being bound by theory, it is believed that the efficacy against HIV infection is not due to cytotoxicity. Cells were still viable at the highest concentration tested (25 μM).

Example

Figure 3:
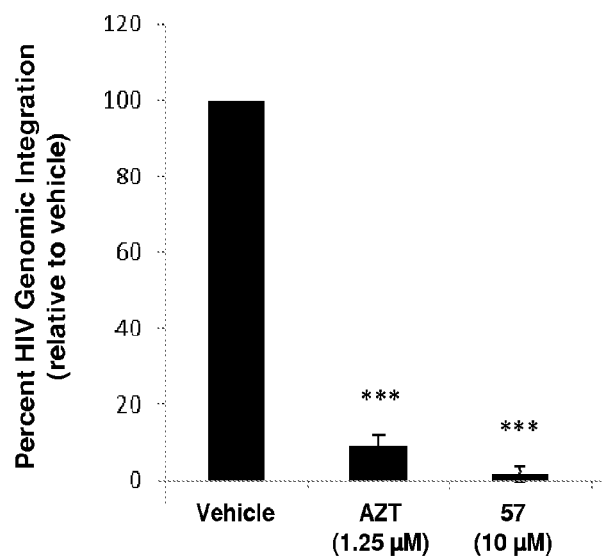
FIG. 3 shows that Example 57 significantly inhibits HIV viral integration.
Figure 4A:
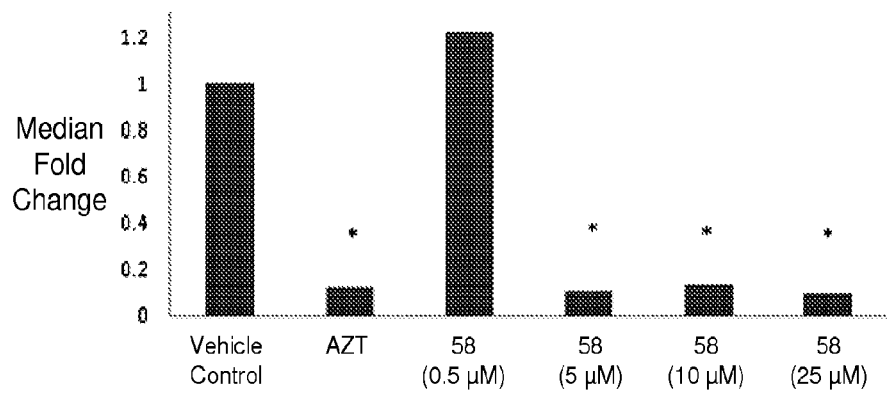
FIGS. 4A, 4B, 4C, and 4D show the activity of illustrative Examples 58, 59, 60 and 65, respectively, against HIV compared to AZT control.
Figure 4B:
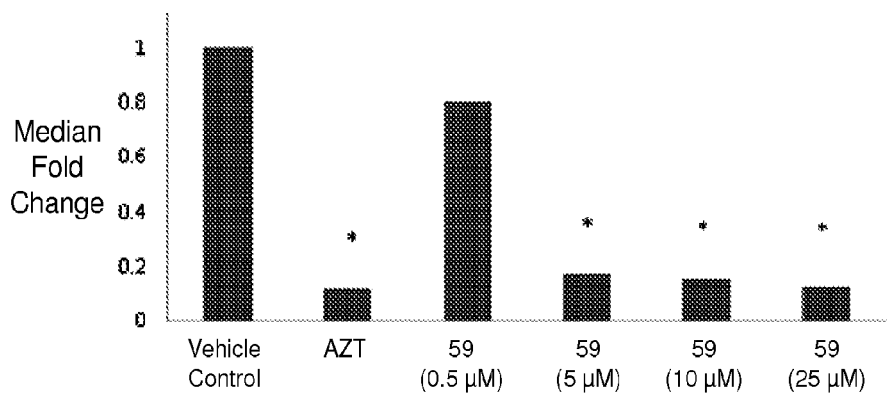
Figure 4C:
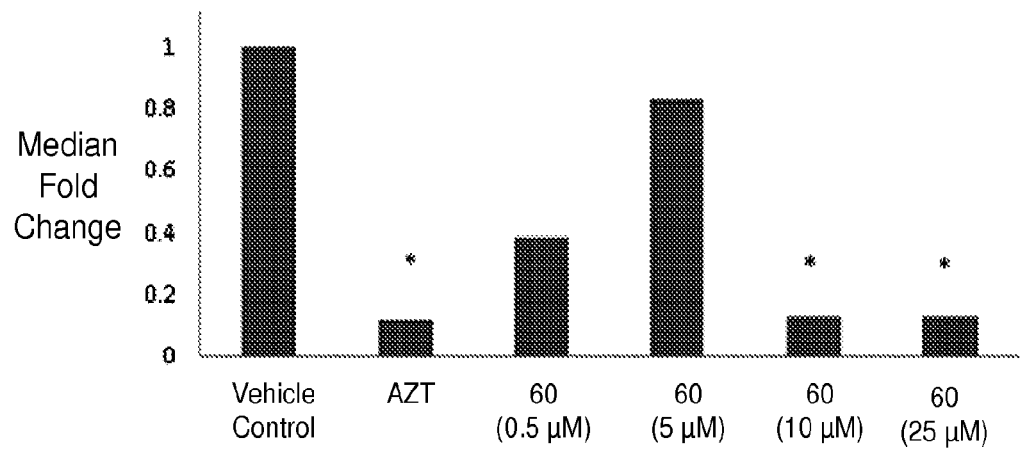
Figure 4D:
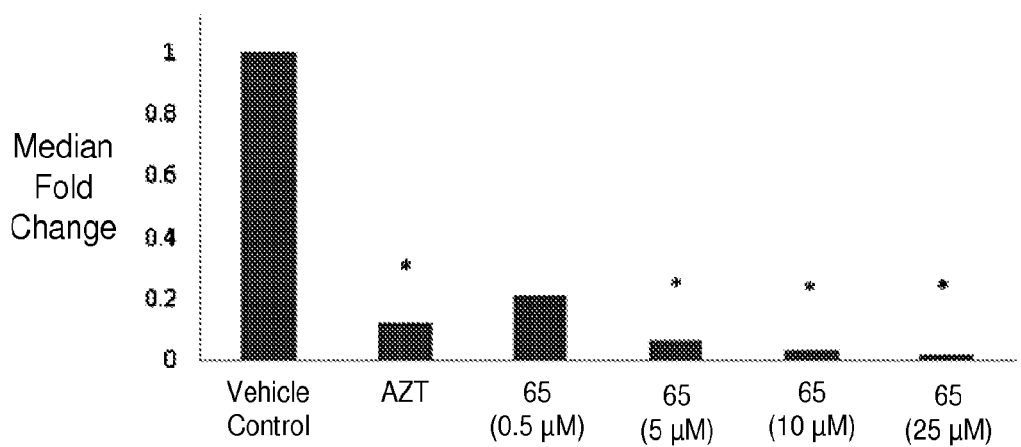

HIV Genomic DNA Integration. Compounds described herein show inhibition at the viral integration. Stimulated PBMCs are infected with HIV-Bal (2 ng/mL per $10^6$ cells) for 5 h. The PBMCs are then treated with compounds at desired concentrations and AZT (control) for 72 h post-infection. The cells are then washed three times with media. Genomic DNA is prepared from samples using DNeasy Blood and Tissue Kit (Qiagen). ALU-PCR is performed followed by real time PCR to quantify integrated viral genome. The following primers are used to amplify HIV transcripts: HIV LTR, Forward 5'-TCAAGTGAGTGC-CCGGTT (SEQ ID NO: 1) and Reverse 5'-AGCTCCG-GTTTCTCTTTCGCT (SEQ ID NO: 2) and GAPDH—Forward 5'-TGACTTCAACAGCGACACCCACT (SEQ ID NO: 3) and Reverse 5'-ACCACCCTGTTGCTGTAGC-CAAAT (SEQ ID NO: 4). GADPH is used as endogenous control. AZT (1.25 μM, a reverse transcriptase inhibitor) significantly inhibits HIV viral integration. FIG. 3 shows that Example 57 significantly inhibits viral integration at each concentration. All results represent two independent experiments performed;*=$p<0.05$, =$p<0.01$, *=$p<0.001$ in comparison with vehicle (1.25 μM DMSO).

Example

Figure 5A:
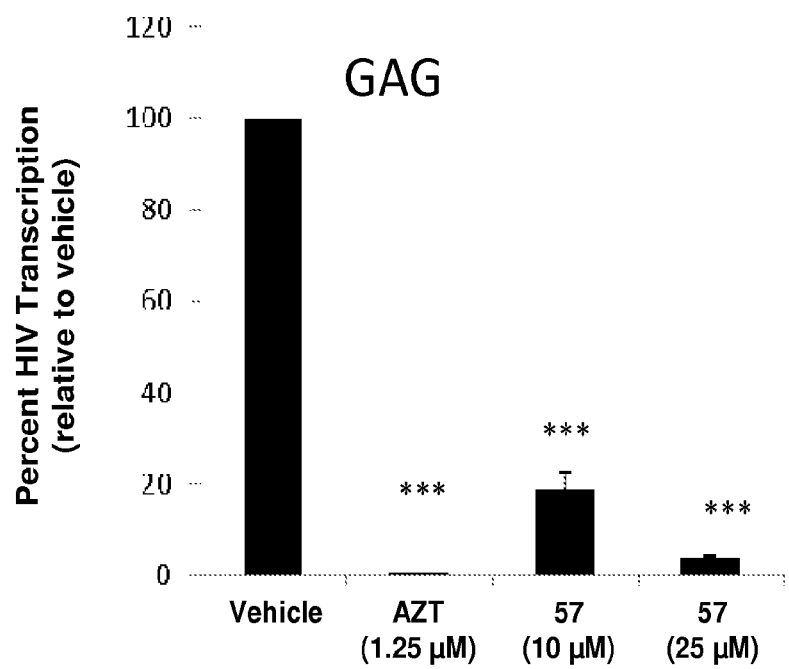
FIGS. 5A, 5B, and 5C show that Example 57 significantly inhibits HIV transcription.
Figure 5B:
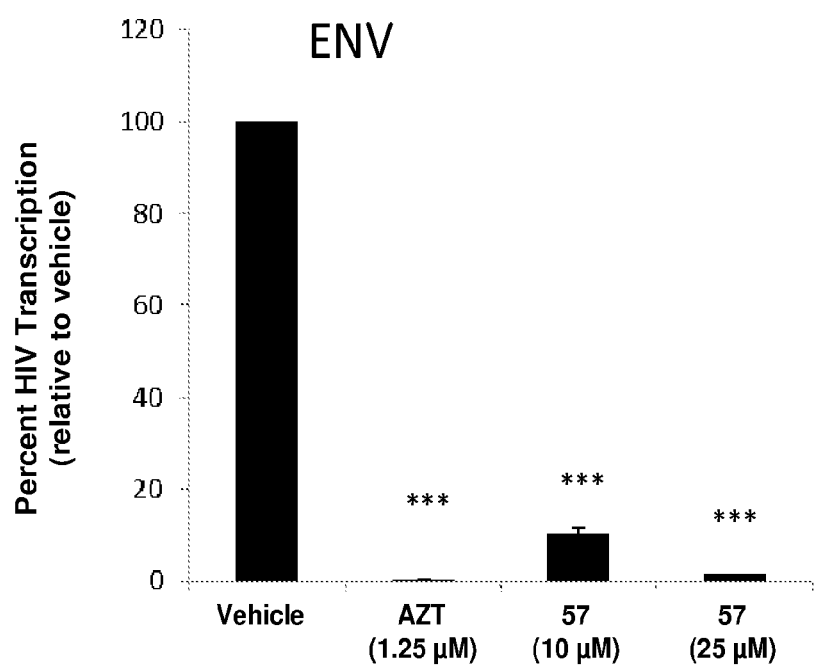
Figure 5C:
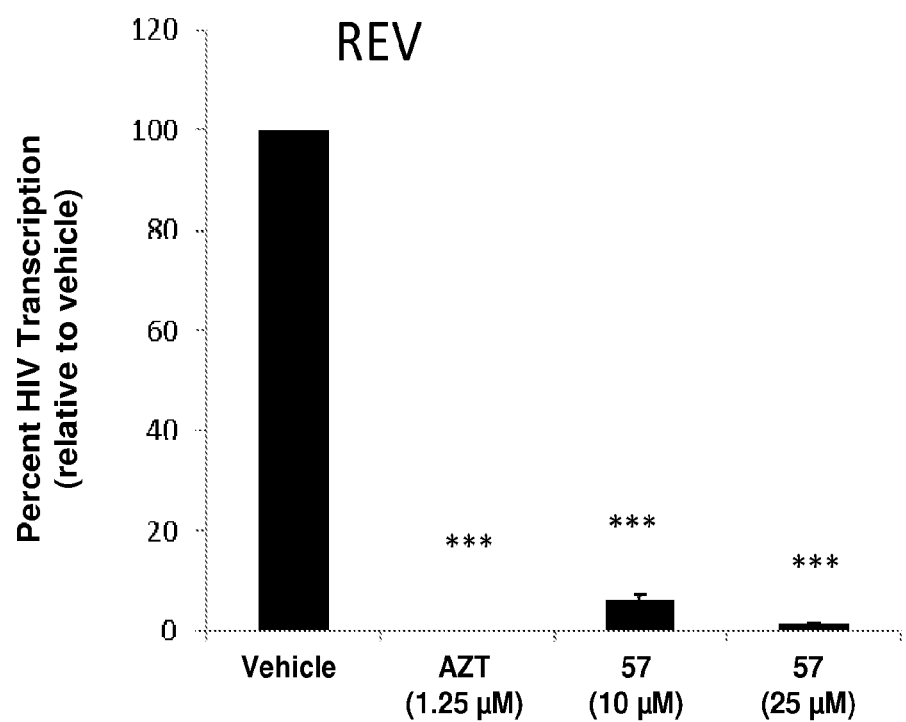
Figure 6:
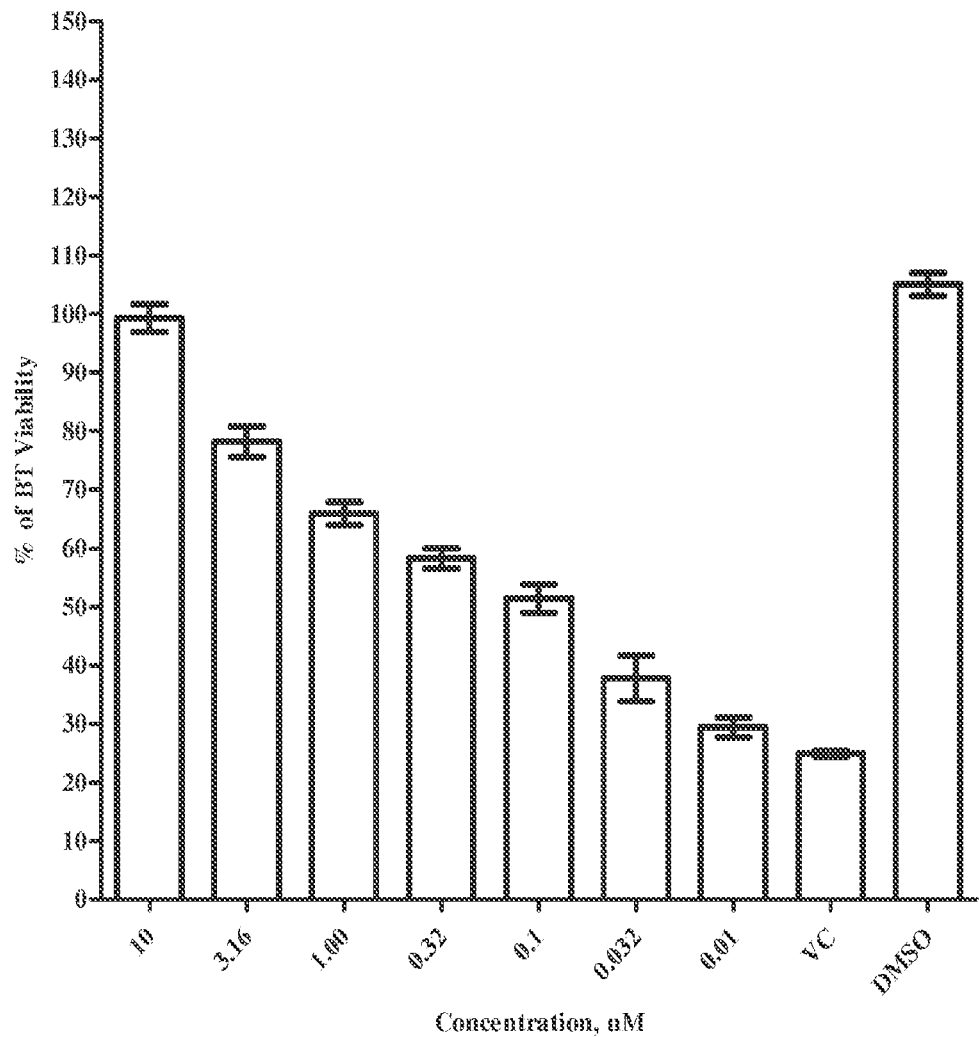
FIG. 6 shows illustrative dose response data for Example 100 against BVDV.
Figure 7:
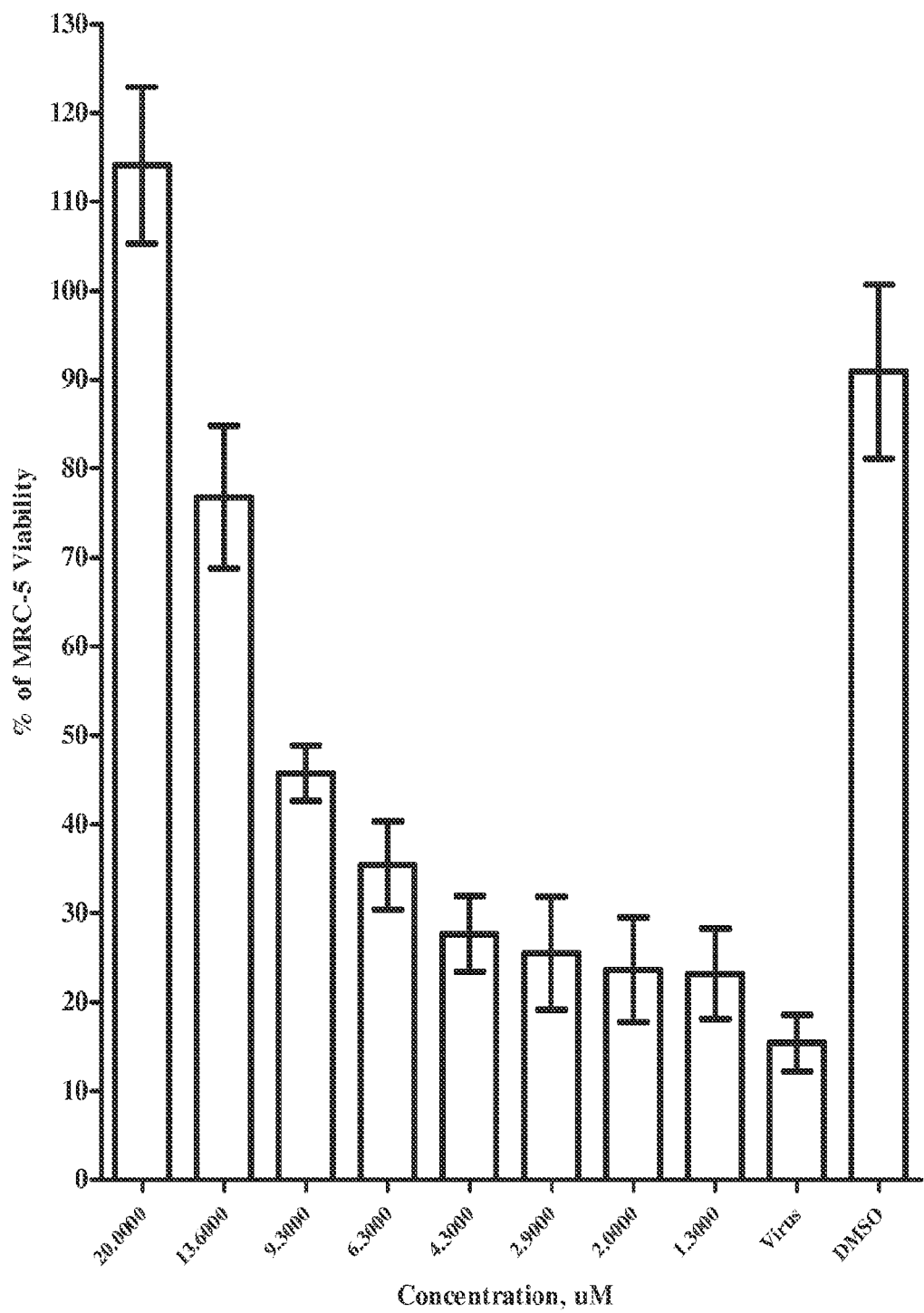
FIG. 7 shows illustrative anti-CV activity of Example 104. The antiviral action was determined by the ability of 104 to reduce CV-induced Cytopathic Effect (CPE) in MRC-5 cells. Doses at and above 2 μM appear to display antiviral activity.

HIV transcription. Compounds inhibit at the viral transcription level. Stimulated PBMCs are infected with HIV-Bal (2 ng/mL per $10^6$ cells) for 4-6 h. PBMCs are then treated with compounds at desired concentrations and AZT (control) for 72 h post-infection. The cells are then washed three times with media and genomic RNA is prepared from samples using RNEasy MiniKit (Qiagen). Real time RT-PCR is performed to detect mature viral early (Rev) and late transcripts (Gag and Env). The following primers are used to amplify HIV transcripts: Rev, Forward 5'-TCCTTG-GCACTTATCTGGGACGAT (SEQ ID NO: 7) and Reverse 5'-TCCCAGAAGTTCCACAATCCTCGT (SEQ ID NO: 8); Env, Forward 5'-ACGAGGATTGTGGAACTTCTGGGA (SEQ ID NO: 9) and Reverse 5'-TGGCATTGAG-CAAGCTAACAGCAC (SEQ ID NO: 10); Gag, Forward 5'-AGAGAAGGCTTTCAGCCCAGAAGT (SEQ ID NO: 11) and Reverse 5'-TGCACTGGATGCACTCTATCCCAT (SEQ ID NO: 12); GAPDH, Forward 5'-TGACTTCAACA-GCGACACCCACT (SEQ ID NO: 3) and Reverse 5'-AC-CACCCTGTTGCTGTAGCCAAAT (SEQ ID NO: 4). GADPH is used as endogenous control. AZT (1.25 μM, a reverse transcriptase inhibitor) significantly inhibits HIV transcription. FIGS. 5A, 5B, and 5C show that Example 57 significantly inhibits viral transcription at each concentration. All results represent two independent experiments performed; ***=$p<0.001$ in comparison with vehicle (1.25 μM DMSO).

Example

Assay for Anti-BVDV efficacy. Bovine Turbinate (BT) cells maintained as monolayers in disposable cell culture labware are used for the antiviral efficacy test. Prior to testing, host cell cultures are seeded onto the 96-well cell culture plates and used approximately 48 hours after seeding. Cells are cultured to achieve monolayers of 80-90% confluence. The growth medium (GM) and maintenance medium (MM) include Dulbecco's Modified Eagle Media (DMEM) with L-glutamine (ATCC #30-2002), 10% Horse serum and penicillin/streptomycin (10,000 units of penicillin and 10,000 μg of streptomycin per mL, Life Technologies #15140-122 or similar) for a final concentration of 100 units penicillin and 100 μg streptomycin in the medium.

Bovine Viral Diarrhea Virus strain NADL from BSLI high-titer virus stock is used. Prior to use, aliquots of the stock virus are removed and thawed from a −70° C. freezer. The BVDV is diluted in a maintenance medium (MM) to obtain 0.1 Multiplicity of Infection (MOI).

Example

Cytopathic (CPE) assay. CPE refers to degenerative changes in BT tissue culture induced by BVDV as a consequence of its multiplication. BT cell cultures are washed with PBS, and 100 μL aliquots of MM are added to the cells and incubated in a $CO_2$ incubator for 2 hours. After incubation, the MM is removed; the cells washed again with PBS and overlaid with 100 μL of the different concentrations of test compounds. The plates are incubated in a $CO_2$ incubator for 48 to 72 hours. Upon completion of incubation, the plates are evaluated for test compound-induced inhibition of CPE using the 3-(4,5-dimethylthiazol-2-yl)-2,5-diphenyltetrazolium bromide, a yellow tetrazole (MTT) assay. This assay is a colorimetric assay that measures the activity of enzymes that reduce MTT to the purple color formazan dye. CPE is confirmed using an Inverted Compound Microscope.

Prior to the CPE assays, test compounds are tested to determine the highest non-cytotoxic concentration. Cell cultures are washed with PBS, overlaid with 100 μL of MM and incubated for 2 hours. After incubation, the MM is replaced with 100 μL aliquots of the test compounds at different concentrations. The cytotoxicity test includes a DMSO control (dose not to exceed 0.5%). The plates are incubated in a $CO_2$ incubator for 48 to 72 hours. Toxicity is evaluated using the MTT assay. The tests and assays are performed twice in duplicates. Results showing a significant difference are repeated two more times.

Example

MTS (Cell Viability) assay. Test compounds are also evaluated in a conventional cytotoxicity assay. Uninfected and stimulated PBMCs are plated in a 96 well flat-bottom plate at 200,000 cells in 200 μL volume of the media in quadruplicates for 3 days at 37° C., in a 5% $CO_2$, humidified incubator. 20 μL of CellTiter 96 AQueous One Solution Reagent (Promega) is added to each well of the plate, and the plate is incubated at 37° C., in a 5% $CO_2$, humidified incubator for 3 h. The plate is then read on a plate reader at 490 nm. The readings are then measured as percentage of viability relative to the control. It is appreciated that the lack of cyctoxicity supports the conclusion that the test compound activity in reducing viral titer is specific to the viral disease.

Example

The compounds and antiviral activities in Table 4 are described herein. In each of the compounds described herein, it is to be understood that each atom includes a full valence, where each remaining atom is hydrogen. All Example compounds tested at multiple doses show a dose response. Illustrative compounds and associated antiviral activity are shown in the following tables.

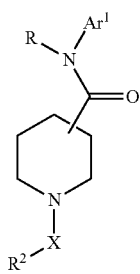

TABLE 4(a)

| Example | Ar¹ | R | Ring Connection | X | R² | BVDV Antiviral Activity |
|---|---|---|---|---|---|---|
| 57 | 3-indol-2-yl-Ph | H | C4 | C(O) | C≡C—CH₃ | +++ |
| 58 (427) | 4-benzimidazol-2-yl-Ph | H | C4 | CH2 | 3-MeO—Ph | +++ |

TABLE 4(a)-continued

| Example | Ar¹ | R | Ring Connection | X | R² | BVDV Antiviral Activity |
|---|---|---|---|---|---|---|
| 59 (252) | 4-benzimidazol-2-yl-Ph | H | C4 | CH2 | 5-Et-furan-2-yl | ++ |
| 60 (308) | 3-indol-2-yl-Ph | H | C4 | C(O) | thiazol-5-yl | +++ |
| 65 (P107/765) | 4-benzimidazol-2-yl-Ph | H | C4 | CH2 | 3-MeO—Ph | +++ |
| 99 | 4-(Benzimidazol-2-yl)Ph | H | C4 | — | [pyrrolopyrimidine-Me structure] | +++ |
| 100 (2A) | 3-(Indol-2-yl)Ph | H | C4 | — | [pyrrolopyrimidine-Me structure] | +++ |
| 101 | 4-(2-F—PhO)Ph | H | C4 | — | [pyrrolopyrimidine-Me structure] | ++ |
| 102 (4A) | 3-(3-F—Ph)Ph | H | C4 | — | [pyrrolopyrimidine-Me structure] | +++ |
| 103 | 3-Br—Ph | H | C4 | — | [pyrrolopyrimidine-Me structure] | + |

Antiviral Activity: Cell survival compared to untreated control.

"+" corresponds to ≤50 cell survival at 10 μM, and improved survival over untreated control "++" corresponds to >50 but <75 cell survival at 10 μM "+++" corresponds to ≥75 cell survival at 10 μM

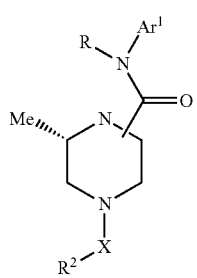

TABLE 4(b)

| Example | Ar¹ | R | Ring Connection | X | R² | BVDV Antiviral Activity |
|---|---|---|---|---|---|---|
| 104 (4B) | 4-(Benzimidazol-2-yl)Ph | H | N1 | $CH_2$ | Quinolin-8-yl | +++ |
| 105 | 4-(Benzimidazol-2-yl)Ph | H | N1 | $CH_2$ | 5-Et-furan-2-yl | + |
| 106 | 3-(Indol-2-yl)Ph | H | N1 | C(O) | C≡C—CH3 | + |
| 107 | 3-(Indol-2-yl)Ph | H | N1 | C(O) | Thiazol-5-yl | +++ |
| 108 | 3-Br—Ph | H | N1 | — | 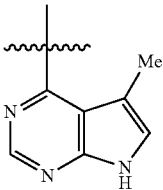 [SMILES: *c1ncnc2[nH]cc(C)c12] | + |

Antiviral Activity: Cell survival compared to untreated control.
"+" corresponds to ≤50 cell survival at 10 μM, and improved survival over untreated control
"++" corresponds to >50 but <75 cell survival at 10 μM
"+++" corresponds to ≥75 cell survival at 10 μM Example Human lung fibroblast (MRC-5 cells) cytotoxicity assay. MRC-5 cells cultures are washed with PBS, and incubated with 100 μl aliquots of medium (EMEM with 2% Fetal Bovine Serum). After 2 hours of incubation, the medium is removed and the cells are washed with PBS, treated with 100 μl of medium containing test compound at different concentrations and incubated for additional 72 hours. After this incubation, the plates are evaluated for cell toxicity using the MTT assay. The results are presented as percent reduction in cell viability where 100% is DMSO control without test compound.

Example

Coronavirus antiviral assay. MRC-5 cells at 70-80% confluency are washed with phosphate buffered saline (PBS), infected with 100 μl aliquots of medium containing the human Coronavirus 229E strain at 0.1 MOI and then incubated in a $CO_2$ incubator for 2 hours to allow virus adsorption. The incubation temperature is 35° C.±2° C. After incubation, the virus inoculum is removed and the infected cells are washed with PBS, treated with 100 μl medium containing test compound at the different concentrations and incubated for additional 72 hours. After incubation, the plates are evaluated for Coronavirus 229E strain-induced CPE using the colormetric MTT (3-(4,5-dimethylthiazolyl-2)-2,5-diphenyltetrazolium bromide) assay. This test measures cell viability by assessing the ability of enzymes released from damaged cells to reduce the tetrazolium dye into its purple colored formazan derivative. The results are presented as percent inhibition of CPE where 100% inhibition of CPE caused by the virus is approximately equal to the mean of the DMSO control, without test compound. In all the studies, the final concentration of DMSO in the medium was 0.5%. The assay is performed in 96-well cell culture flat bottom plates.

Each compound showed an improved cell viability over untreated viral control. Results for illustrative compounds are shown in the following table

| Example | CV activity |
|---|---|
| 100 (2A) | >50% at 4 μM |
| 102 (4A) | >30% at 4 μM |
| 104 (4B) | >70% at 14 μM |

The following publications, and each additional publication cited herein, are incorporated herein by reference.

Sepkowitz, "AIDS—the first 20 years" N Engl J Med 344(23):1764-72 (2001).

Weiss, "How does HIV cause AIDS?" Science 260(5112): 1273-9 (1993).

Dybul et al., Panel on Clinical Practices for Treatment of HIV "Guidelines for using antiretroviral agents among HIV-infected adults and adolescents" Ann Intern Med 137(5 Pt 2):381-433 (2002).

Martinez-Picado et al., "Antiretroviral resistance during successful therapy of human immunodeficiency virus type 1 infection" Proc Natl Acad Sci USA 97(20):10948-10953 (2000).

Cory et al., "Use of an aqueous soluble tetrazolium/formazan assay for cell growth assays in culture" Cancer Commun 3(7):207-212 (1991); ISSN 0955-3541; PMID 1867954.

Hashida et al., "More reliable diagnosis of infection with human immunodeficiency virus type 1 (HIV-1) by detection of antibody IgGs to pol and gag proteins of HIV-1 and p24 antigen of HIV-1 in urine, saliva, and/or serum with highly sensitive and specific enzyme immunoassay (immune complex transfer enzyme immunoassay)" J Clin Lab Anal (5):267-86 (1997). Erratum in: J Clin Lab Anal (1):76 (1998).

Hagemeijer et al., "Biogenesis and dynamics of the coronavirus replicative structures" Viruses 4(11):3245-69 (2012).

Belouzard et al., "Mechanisms of coronavirus cell entry mediated by the viral spike protein" Viruses 4(6):1011-33 (2012).

Satija et al., "The molecular biology of SARS coronavirus" Ann N Y Acad Sci. 1102:26-38 (2007).

Weiss et al., "Coronavirus pathogenesis" Adv Virus Res 81:85-164 (2011).

Kupferschmidt, "Emerging diseases, Researchers scramble to understand camel connection to MERS" Science 341 (6147):702 (2013).

Lu et al., "Middle East respiratory syndrome coronavirus (MERS-CoV): challenges in identifying its source and controlling its spread" Microbes Infect 15(8-9):625-9 (2013).

What is claimed is:

1. A method for treating an HCV or BVDV infection in a host animal, the method comprising the step of administering to the host animal a therapeutically effective amount of one or more compounds of the formula

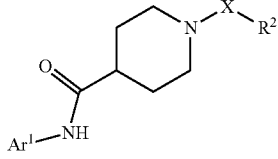

or a pharmaceutically acceptable salt thereof; and wherein:

the one of more compounds each comprise a combination mode of $Ar^1$, X, and $R^2$, said combination mode selected from the group consisting of:

| Combination Mode | $Ar^1$ | X | $R^2$ |
|---|---|---|---|
| 1 | 3-(3-$FC_6H_4$)$C_6H_4$ | $CH_2$ | Quinolin-8-yl |
| 2 | 4-(3-Me$C_6H_4$)$C_6H_4$ | $CH_2$ | 4-OH-3-MeO—$C_6H_3$ |
| 3 | 4-(2-$FC_6H_4$O)$C_6H_4$ | $CH_2$ | 2-OH-4-MeO—$C_6H_3$ |
| 4 | 2-(3-MeO$C_6H_4$)$C_6H_4$ | $CH_2$ | Quinolin-8-yl |
| 5 | 4-(Benzimidazol-2-yl)$C_6H_4$ | $CH_2$ | 2-MeO—$C_6H_4$ |
| 6 | 2-(3-MeO$C_6H_4$)$C_6H_4$ | $CH_2$ | 4-OH-3,5-$Me_2$—$C_6H_2$ |
| 7 | 2-(3-MeO$C_6H_4$)$C_6H_4$ | $CH_2$ | 2-MeO—$C_6H_4$ |
| 8 | 3-(3-$FC_6H_4$)$C_6H_4$ | $CH_2$ | 4-OH—$C_6H_4$ |
| 9 | 3-(3-$FC_6H_4$)$C_6H_4$ | $CH_2$ | 2-(n-Bu)-imidazol-4-yl |
| 10 | 4-(2-$FC_6H_4$O)$C_6H_4$ | $CH_2$ | 2,3-Methylenedioxy-$C_6H_3$ |
| 11 | 3-(3-$FC_6H_4$)$C_6H_4$ | $CH_2$ | 3-OH—$C_6H_4$ |
| 12 | 3-(3-$FC_6H_4$)$C_6H_4$ | $CH_2$ | 2-OH-6-MeO—$C_6H_3$ |
| 13 | 3-(3-Cl$C_6H_4$)$C_6H_4$ | $CH_2$ | 4-OH—$C_6H_4$ |
| 14 | 2-(3-MeO$C_6H_4$)$C_6H_4$ | $CH_2$ | 3-Me-4-MeO—$C_6H_3$ |
| 15 | 2-(3-MeO$C_6H_4$)$C_6H_4$ | $CH_2$ | 3-MeO—$C_6H_4$ |
| 16 | 2-(3-MeO$C_6H_4$)$C_6H_4$ | $CH_2$ | 4-F-2-MeO—$C_6H_3$ |
| 17 | 3-(2-Indolyl)$C_6H_4$ | $CH_2$ | (1-i-Pr-pyrazol-4-yl) |
| 18 | 2-(3-MeO$C_6H_4$)$C_6H_4$ | $CH_2$ | t-Bu |
| 19 | 3-(2-Furyl)$C_6H_4$ | $CH_2$ | Quinolin-8-yl |
| 20 | 3-(2-Me-1,3,4-thiazol-5-yl)$C_6H_4$ | C(=O) | 2-Furyl |
| 21 | 3-(3-Cl$C_6H_4$)$C_6H_4$ | $CH_2$ | 4-OH-3-MeO—$C_6H_3$ |
| 22 | 3-indol-2-yl$C_6H_4$ | C(O) | C≡C—$CH_3$ |
| 23 | 4-benzimidazol-2-yl$C_6H_4$ | $CH_2$ | 3-MeO—$C_6H_4$ |
| 24 | 4-benzimidazol-2-yl$C_6H_4$ | $CH_2$ | 5-Et-furan-2-yl |
| 25 | 3-indol-2-yl$C_6H_4$ | C(O) | thiazol-5-yl |
| 26 | 4-(2-$FC_6H_4$O)$C_6H_4$ | $CH_2$ | 2-HO-3-MeO—$C_6H_3$ |
| 27 | 2-(3-MeO$C_6H_4$)$C_6H_4$ | $CH_2$ | 2-HO-3-MeO—$C_6H_3$ |
| 28 | 3-(3-Cl$C_6H_4$)$C_6H_4$ | $CH_2$ | 2-HO-3-MeO—$C_6H_3$ |
| 29 | 4-(2-$FC_6H_4$O)$C_6H_4$ | $CH_2$ | Et |
| 30 | 4-benzimidazol-2-yl$C_6H_4$ | $CH_2$ | 3-MeO—$C_6H_4$ |
| 31 | 4-(3,5-$Me_2$-pyrazol-1-yl)$C_6H_4$ | $CH_2CH=CH$ (E) | 2-MeO—$C_6H_4$ |
| 32 | 3-(3-$FC_6H_4$)$C_6H_4$ | $CH_2$ | 2-Et-5-Me-imidazol-4-yl |
| 33 | 3-(3-MeO$C_6H_4$)$C_6H_4$ | $CH_2$ | CH=C(Me)$_2$ |
| 34 | 4-(2-$FC_6H_4$O)$C_6H_4$ | $CH_2$ | 3-MeO—$C_6H_4$ |
| 35 | 2-(3-MeO$C_6H_4$)$C_6H_4$ | $CH_2$ | naphtha-1-yl |
| 36 | 3-(3-Cl$C_6H_4$)$C_6H_4$ | $CH_2$ | 1-allyl-3-Me-pyrazol-4-yl |
| 37 | 4-(2-$FC_6H_4$O)$C_6H_4$ | $CH_2$ | 1-Pr-5-Me-pyrazol-4-yl |
| 38 | 4-(2-$FC_6H_4$O)$C_6H_4$ | $CH_2$ | Me |
| 39 | 4-(2-$FC_6H_4$O)$C_6H_4$ | — | 1-Et-piperidin-4-yl |
| 40 | 3-(3-$FC_6H_4$)$C_6H_4$ | $CH_2$ | 1-(i-Pr)-3,5-$Me_2$-pyrazol-4-yl |
| 41 | 2-PhO-pyridin-5-yl | $CH_2$ | Ph |
| 42 | 3-(3-Cl$C_6H_4$)$C_6H_4$ | $CH_2$ | 1-Et-pyrazol-4-yl |
| 43 | 3-(3-$FC_6H_4$)$C_6H_4$ | $CH_2$ | 3,5,6-$Me_3$-pyrazin-2-yl |
| 44 | 2-(3-MeO$C_6H_4$)$C_6H_4$ | $CH_2$ | 1-Pr-5-Me-pyrazol-4-yl |
| 45 | 4-(2-$FC_6H_4$O)$C_6H_4$ | $CH_2$ | 2-HO-5-MeO—$C_6H_3$ |
| 46 | 3-(3-Cl$C_6H_4$)$C_6H_4$ | $CH_2$ | 1-(i-Pr)-pyrazol-4-yl |
| 47 | 2-PhO-pyridin-5-yl | $CH_2$ | 5-Cl-thien-2-yl |
| 48 | 3-(3-$FC_6H_4$)$C_6H_4$ | $CH_2$ | 2,3-(MeO)$_2$—$C_6H_3$ |
| 49 | 4-(2-$FC_6H_4$O)$C_6H_4$ | $CH_2$ | 4-HO-3-MeO—$C_6H_3$ |
| 50 | 4-(2-$FC_6H_4$O)$C_6H_4$ | $CH_2$ | 5-(i-Bu)-pyrazol-3-yl |
| 51 | 2-(3-MeO$C_6H_4$)$C_6H_4$ | $CH_2$ | 3,5,6-$Me_3$-pyrazin-2-yl |
| 52 | 2-(3-MeO$C_6H_4$)$C_6H_4$ | $CH_2$ | 2,5-$Me_2$—$C_6H_3$ |
| 53 | 3-(3-$FC_6H_4$)$C_6H_4$ | $CH_2$ | Benzo-2,1,3-thiadiazol-5-yl |
| 54 | 3-(3-$FC_6H_4$)$C_6H_4$ | $CH_2$ | 2-HO-3-MeO—$C_6H_3$ |
| 55 | 4-(benzimidazol-2-yl)$C_6H_4$ | $CH_2$ | Cyclohexen-4-yl |
| 56 | 3-(3-$FC_6H_4$)$C_6H_4$ | $CH_2$ | 1-allyl-3-Me-pyrazol-4-yl |
| 57 | 4-(2-$FC_6H_4$O)$C_6H_4$ | $CH_2$ | 5-Me-furan-2-yl |
| 58 | 3-(3-$FC_6H_4$)$C_6H_4$ | $CH_2$ | 1-Et-5-Me-pyrazol-4-yl |
| 59 | 4-(benzimidazol-2-yl)$C_6H_4$ | $CH_2$ | 3-$FC_6H_3$ |
| 60 | 4-(2-$FC_6H_4$O)$C_6H_4$ | $CH_2$ | 1-Et-pyrazol-4-yl |
| 61 | 3-(3-Cl$C_6H_4$)$C_6H_4$ | $CH_2$ | Pyridin-2-yl |
| 62 | 4-(Benzimidazol-2-yl)Ph | — | 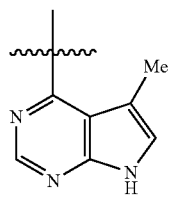 [SMILES: *c1ncnc2[nH]cc(C)c12] |
| 63 | 3-(Indol-2-yl)Ph | — | 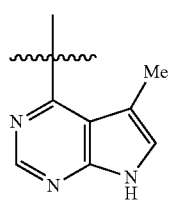 [SMILES: *c1ncnc2[nH]cc(C)c12] |

| Combination Mode | Ar¹ | X | R² |
|---|---|---|---|
| 64 | 4-(2-F—PhO)Ph | — | 4-(7H-pyrrolo[2,3-d]pyrimidin-4-yl), 5-Me |
| 65 | 3-(3-F—Ph)Ph | — | 4-(7H-pyrrolo[2,3-d]pyrimidin-4-yl), 5-Me |
| 66 | 3-Br—Ph | — | 4-(7H-pyrrolo[2,3-d]pyrimidin-4-yl), 5-Me | and one or more pharmaceutically acceptable carriers, excipients, or diluents, or combinations thereof.

2. The method of claim 1, wherein the viral infection is a HCV infection.

3. The method of claim 1, wherein the viral infection is a BVDV infection.

4. The method of claim 1, wherein the one of more compounds each comprise a combination mode of Ar¹, X, and R², said combination mode selected from the group consisting of:

| Combination Mode | Ar¹ | X | R² |
|---|---|---|---|
| 1 | 3-(3-FC$_6$H$_4$)C$_6$H$_4$ | CH$_2$ | Quinolin-8-yl |
| 3 | 4-(2-FC$_6$H$_4$O)C$_6$H$_4$ | CH$_2$ | 2-OH-4-MeO—C$_6$H$_3$ |
| 4 | 2-(3-MeOC$_6$H$_4$)C$_6$H$_4$ | CH$_2$ | Quinolin-8-yl |
| 5 | 4-(Benzimidazol-2-yl)C$_6$H$_4$ | CH$_2$ | 2-MeO—C$_6$H$_4$ |
| 6 | 2-(3-MeOC$_6$H$_4$)C$_6$H$_4$ | CH$_2$ | 4-OH-3,5-Me$_2$—C$_6$H$_2$ |
| 7 | 2-(3-MeOC$_6$H$_4$)C$_6$H$_4$ | CH$_2$ | 2-MeO—C$_6$H$_4$ |
| 8 | 3-(3-FC$_6$H$_4$)C$_6$H$_4$ | CH$_2$ | 4-OH—C$_6$H$_4$ |
| 9 | 3-(3-FC$_6$H$_4$)C$_6$H$_4$ | CH$_2$ | 2-(n-Bu)-imidazol-4-yl |
| 10 | 4-(2-FC$_6$H$_4$O)C$_6$H$_4$ | CH$_2$ | 2,3-Methylenedioxy-C$_6$H$_3$ |
| 22 | 3-indol-2-ylC$_6$H$_4$ | C(O) | C≡C—CH$_3$ |
| 23 | 4-benzimidazol-2-ylC$_6$H$_4$ | CH$_2$ | 3-MeO—C$_6$H$_4$ |
| 24 | 4-benzimidazol-2-ylC$_6$H$_4$ | CH$_2$ | 5-Et-furan-2-yl |
| 26 | 4-(2-FC$_6$H$_4$O)C$_6$H$_4$ | CH$_2$ | 2-HO-3-MeO—C$_6$H$_3$ |
| 27 | 2-(3-MeOC$_6$H$_4$)C$_6$H$_4$ | CH$_2$ | 2-HO-3-MeO—C$_6$H$_3$ |
| 28 | 3-(3-ClC$_6$H$_4$)C$_6$H$_4$ | CH$_2$ | 2-HO-3-MeO—C$_6$H$_3$ |
| 29 | 4-(2-FC$_6$H$_4$O)C$_6$H$_4$ | CH$_2$ | Et |
| 30 | 4-benzimidazol-2-ylC$_6$H$_4$ | CH$_2$ | 3-MeO—C$_6$H$_4$ |
| 33 | 3-(3-MeOC$_6$H$_4$)C$_6$H$_4$ | CH$_2$ | CH=C(Me)$_2$ |
| 38 | 4-(2-FC$_6$H$_4$O)C$_6$H$_4$ | CH$_2$ | Me |
| 39 | 4-(2-FC$_6$H$_4$O)C$_6$H$_4$ | — | 1-Et-piperidin-4-yl |
| 40 | 3-(3-FC$_6$H$_4$)C$_6$H$_4$ | CH$_2$ | 1-(i-Pr)-3,5-Me$_2$-pyrazol-4-yl |
| 41 | 2-PhO-pyridin-5-yl | CH$_2$ | Ph |
| 42 | 3-(3-ClC$_6$H$_4$)C$_6$H$_4$ | CH$_2$ | 1-Et-pyrazol-4-yl |
| 43 | 3-(3-FC$_6$H$_4$)C$_6$H$_4$ | CH$_2$ | 3,5,6-Me$_2$-pyrazin-2-yl |
| 45 | 4-(2-FC$_6$H$_4$O)C$_6$H$_4$ | CH$_2$ | 2-HO-5-MeO—C$_6$H$_3$ |
| 47 | 2-PhO-pyridin-5-yl | CH$_2$ | 5-Cl-thien-2-yl |
| 49 | 4-(2-FC$_6$H$_4$O)C$_6$H$_4$ | CH$_2$ | 4-HO-3-MeO—C$_6$H$_3$ |
| 51 | 2-(3-MeOC$_6$H$_4$)C$_6$H$_4$ | CH$_2$ | 3,5,6-Me$_3$-pyrazin-2-yl |
| 54 | 3-(3-FC$_6$H$_4$)C$_6$H$_4$ | CH$_2$ | 2-HO-3-MeO—C$_6$H$_3$ |
| 56 | 3-(3-FC$_6$H$_4$)C$_6$H$_4$ | CH$_2$ | 1-allyl-3-Me-pyrazol-4-yl |
| 58 | 3-(3-FC$_6$H$_4$)C$_6$H$_4$ | CH$_2$ | 1-Et-5-Me-pyrazol-4-yl |
| 60 | 4-(2-FC$_6$H$_4$O)C$_6$H$_4$ | CH$_2$ | 1-Et-pyrazol-4-yl |
| 62 | 4-(Benzimidazol-2-yl)Ph | — | 4-(7H-pyrrolo[2,3-d]pyrimidin-4-yl), 5-Me |
| 63 | 3-(Indol-2-yl)Ph | — | 4-(7H-pyrrolo[2,3-d]pyrimidin-4-yl), 5-Me |
| 64 | 4-(2-F—PhO)Ph | — | 4-(7H-pyrrolo[2,3-d]pyrimidin-4-yl), 5-Me |
| 65 | 3-(3-F—Ph)Ph | — | 4-(7H-pyrrolo[2,3-d]pyrimidin-4-yl), 5-Me |

5. The method of claim 1, wherein the one of more compounds each comprise a combination mode of Ar¹, X, and R², said combination mode selected from the group consisting of:

| Combination Mode | Ar¹ | X | R² |
|---|---|---|---|
| 3 | 4-(2-FC$_6$H$_4$O)C$_6$H$_4$ | CH$_2$ | 2-OH-4-MeO—C$_6$H$_3$ |
| 4 | 2-(3-MeOC$_6$H$_4$)C$_6$H$_4$ | CH$_2$ | Quinolin-8-yl |
| 5 | 4-(Benzimidazol-2-yl)C$_6$H$_4$ | CH$_2$ | 2-MeO—C$_6$H$_4$ |
| 6 | 2-(3-MeOC$_6$H$_4$)C$_6$H$_4$ | CH$_2$ | 4-OH-3,5-Me$_2$—C$_6$H$_2$ |
| 39 | 4-(2-FC$_6$H$_4$O)C$_6$H$_4$ | — | 1-Et-piperidin-4-yl |

-continued

| Combination Mode | Ar¹ | X | R² |
|---|---|---|---|
| 62 | 4-(Benzimidazol-2-yl)Ph | — | 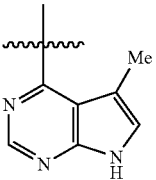 [SMILES: *c1ncnc2[nH]cc(C)c12] |
| 63 | 3-(Indol-2-yl)Ph | — | 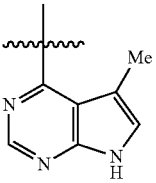 [SMILES: *c1ncnc2[nH]cc(C)c12] |

-continued

| Combination Mode | Ar¹ | X | R² |
|---|---|---|---|
| 65 | 3-(3-F—Ph)Ph | — | 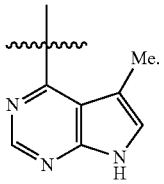 [SMILES: *c1ncnc2[nH]cc(C)c12] |

6. The method of claim 2, wherein the one of more compounds each comprise a combination mode of Ar¹, X, and R², said combination mode selected from the group consisting of:

| Combination Mode | Ar¹ | X | R² |
|---|---|---|---|
| 1 | 3-(3-FC$_6$H$_4$)C$_6$H$_4$ | CH$_2$ | Quinolin-8-yl |
| 2 | 4-(3-MeC$_6$H$_4$)C$_6$H$_4$ | CH$_2$ | 4-OH-3-MeO—C$_6$H$_3$ |
| 3 | 4-(2-FC$_6$H$_4$O)C$_6$H$_4$ | CH$_2$ | 2-OH-4-MeO—C$_6$H$_3$ |
| 4 | 2-(3-MeOC$_6$H$_4$)C$_6$H$_4$ | CH$_2$ | Quinolin-8-yl |
| 5 | 4-(Benzimidazol-2-yl)C$_6$H$_4$ | CH$_2$ | 2-MeO—C$_6$H$_4$ |
| 6 | 2-(3-MeOC$_6$H$_4$)C$_6$H$_4$ | CH$_2$ | 4-OH-3,5-Me$_2$—C$_6$H$_2$ |
| 7 | 2-(3-MeOC$_6$H$_4$)C$_6$H$_4$ | CH$_2$ | 2-MeO—C$_6$H$_4$ |
| 8 | 3-(3-FC$_6$H$_4$)C$_6$H$_4$ | CH$_2$ | 4-OH—C$_6$H$_4$ |
| 9 | 3-(3-FC$_6$H$_4$)C$_6$H$_4$ | CH$_2$ | 2-(n-Bu)-imidazol-4-yl |
| 10 | 4-(2-FC$_6$H$_4$O)C$_6$H$_4$ | CH$_2$ | 2,3-Methylenedioxy-C$_6$H$_3$ |
| 11 | 3-(3-FC$_6$H$_4$)C$_6$H$_4$ | CH$_2$ | 3-OH—C$_6$H$_4$ |
| 12 | 3-(3-FC$_6$H$_4$)C$_6$H$_4$ | CH$_2$ | 2-OH-6-MeO—C$_6$H$_3$ |
| 13 | 3-(3-ClC$_6$H$_4$)C$_6$H$_4$ | CH$_2$ | 4-OH—C$_6$H$_4$ |
| 14 | 2-(3-MeOC$_6$H$_4$)C$_6$H$_4$ | CH$_2$ | 3-Me-4-MeO—C$_6$H$_3$ |
| 15 | 2-(3-MeOC$_6$H$_4$)C$_6$H$_4$ | CH$_2$ | 3-MeO—C$_6$H$_4$ |
| 16 | 2-(3-MeOC$_6$H$_4$)C$_6$H$_4$ | CH$_2$ | 4-F-2-MeO—C$_6$H$_3$ |
| 17 | 3-(2-Indolyl)C$_6$H$_4$ | CH$_2$ | (1-i-Pr-pyrazol-4-yl) |
| 18 | 2-(3-MeOC$_6$H$_4$)C$_6$H$_4$ | CH$_2$ | t-Bu |
| 19 | 3-(2-Furyl)C$_6$H$_4$ | CH$_2$ | Quinolin-8-yl |
| 20 | 3-(2-Me-1,3,4-thiazol-5-yl)C$_6$H$_4$ | C(=O) | 2-Furyl |
| 21 | 3-(3-ClC$_6$H$_4$)C$_6$H$_4$ | CH$_2$ | 4-OH-3-MeO—C$_6$H$_3$ |
| 22 | 3-indol-2-ylC$_6$H$_4$ | C(O) | C≡C—CH$_3$ |
| 23 | 4-benzimidazol-2-ylC$_6$H$_4$ | CH$_2$ | 3-MeO—C$_6$H$_4$ |
| 24 | 4-benzimidazol-2-ylC$_6$H$_4$ | CH$_2$ | 5-Et-furan-2-yl |
| 25 | 3-indol-2-ylC$_6$H$_4$ | C(O) | thiazol-5-yl |
| 26 | 4-(2-FC$_6$H$_4$O)C$_6$H$_4$ | CH$_2$ | 2-HO-3-MeO—C$_6$H$_3$ |
| 27 | 2-(3-MeOC$_6$H$_4$)C$_6$H$_4$ | CH$_2$ | 2-HO-3-MeO—C$_6$H$_3$ |
| 28 | 3-(3-ClC$_6$H$_4$)C$_6$H$_4$ | CH$_2$ | 2-HO-3-MeO—C$_6$H$_3$ |
| 29 | 4-(2-FC$_6$H$_4$O)C$_6$H$_4$ | CH$_2$ | Et |
| 30 | 4-benzimidazol-2-ylC$_6$H$_4$ | CH$_2$ | 3-MeO—C$_6$H$_4$ |
| 31 | 4-(3,5-Me$_2$-pyrazol-1-yl)C$_6$H$_4$ | CH$_2$CH=CH(E) | 2-MeO—C$_6$H$_4$ |
| 32 | 3-(3-FC$_6$H$_4$)C$_6$H$_4$ | CH$_2$ | 2-Et-5-Me-imidazol-4-yl |
| 33 | 3-(3-MeOC$_6$H$_4$)C$_6$H$_4$ | CH$_2$ | CH=C(Me)$_2$ |
| 34 | 4-(2-FC$_6$H$_4$O)C$_6$H$_4$ | CH$_2$ | 3-MeO—C$_6$H$_4$ |
| 35 | 2-(3-MeOC$_6$H$_4$)C$_6$H$_4$ | CH$_2$ | naphtha-1-yl |
| 36 | 3-(3-ClC$_6$H$_4$)C$_6$H$_4$ | CH$_2$ | 1-allyl-3-Me-pyrazol-4-yl |
| 37 | 4-(2-FC$_6$H$_4$O)C$_6$H$_4$ | CH$_2$ | 1-Pr-5-Me-pyrazol-4-yl |
| 38 | 4-(2-FC$_6$H$_4$O)C$_6$H$_4$ | CH$_2$ | Me |
| 39 | 4-(2-FC$_6$H$_4$O)C$_6$H$_4$ | — | 1-Et-piperidin-4-yl |
| 40 | 3-(3-FC$_6$H$_4$)C$_6$H$_4$ | CH$_2$ | 1-(i-Pr)-3,5-Me$_2$-pyrazol-4-yl |
| 41 | 2-PhO-pyridin-5-yl | CH$_2$ | Ph |
| 42 | 3-(3-ClC$_6$H$_4$)C$_6$H$_4$ | CH$_2$ | 1-Et-pyrazol-4-yl |
| 43 | 3-(3-FC$_6$H$_4$)C$_6$H$_4$ | CH$_2$ | 3,5,6-Me$_3$-pyrazin-2-yl |
| 44 | 2-(3-MeOC$_6$H$_4$)C$_6$H$_4$ | CH$_2$ | 1-Pr-5-Me-pyrazol-4-yl |
| 45 | 4-(2-FC$_6$H$_4$O)C$_6$H$_4$ | CH$_2$ | 2-HO-5-MeO—C$_6$H$_3$ |
| 46 | 3-(3-ClC$_6$H$_4$)C$_6$H$_4$ | CH$_2$ | 1-(i-Pr)-pyrazol-4-yl |
| 47 | 2-PhO-pyridin-5-yl | CH$_2$ | 5-Cl-thien-2-yl |
| 48 | 3-(3-FC$_6$H$_4$)C$_6$H$_4$ | CH$_2$ | 2,3-(MeO)$_2$—C$_6$H$_3$ |
| 49 | 4-(2-FC$_6$H$_4$O)C$_6$H$_4$ | CH$_2$ | 4-HO-3-MeO—C$_6$H$_3$ |
| 50 | 4-(2-FC$_6$H$_4$O)C$_6$H$_4$ | CH$_2$ | 5-(i-Bu)-pyrazol-3-yl |
| 51 | 2-(3-MeOC$_6$H$_4$)C$_6$H$_4$ | CH$_2$ | 3,5,6-Me$_3$-pyrazin-2-yl |
| 52 | 2-(3-MeOC$_6$H$_4$)C$_6$H$_4$ | CH$_2$ | 2,5-Me$_2$-C$_6$H$_3$ |

-continued

| Combination Mode | Ar¹ | X | R² |
|---|---|---|---|
| 53 | 3-(3-FC₆H₄)C₆H₄ | CH₂ | Benzo-2,1,3-thiadiazol-5-yl |
| 54 | 3-(3-FC₆H₄)C₆H₄ | CH₂ | 2-HO-3-MeO—C₆H₃ |
| 55 | 4-(benzimidazol-2-yl)C₆H₄ | CH₂ | Cyclohexen-4-yl |
| 56 | 3-(3-FC₆H₄)C₆H₄ | CH₂ | 1-allyl-3-Me-pyrazol-4-yl |
| 57 | 4-(2-FC₆H₄O)C₆H₄ | CH₂ | 5-Me-furan-2-yl |
| 58 | 3-(3-FC₆H₄)C₆H₄ | CH₂ | 1-Et-5-Me-pyrazol-4-yl |
| 59 | 4-(benzimidazol-2-yl)C₆H₄ | CH₂ | 3-FC₆H₄ |
| 60 | 4-(2-FC₆H₄O)C₆H₄ | CH₂ | 1-Et-pyrazol-4-yl |
| 61 | 3-(3-ClC₆H₄)C₆H₄ | CH₂ | Pyridin-2-yl. |

7. The method of claim 2, wherein the one of more compounds each comprise a combination mode of Ar¹, X, and R², said combination mode selected from the group consisting of:

| Combination Mode | Ar¹ | X | R² |
|---|---|---|---|
| 1 | 3-(3-FC₆H₄)C₆H₄ | CH₂ | Quinolin-8-yl |
| 3 | 4-(2-FC₆H₄O)C₆H₄ | CH₂ | 2-OH-4-MeO—C₆H₃ |
| 4 | 2-(3-MeOC₆H₄)C₆H₄ | CH₂ | Quinolin-8-yl |
| 5 | 4-(Benzimidazol-2-yl)C₆H₄ | CH₂ | 2-MeO—C₆H₄ |
| 6 | 2-(3-MeOC₆H₄)C₆H₄ | CH₂ | 4-OH-3,5-Me₂—C₆H₂ |
| 7 | 2-(3-MeOC₆H₄)C₆H₄ | CH₂ | 2-MeO—C₆H₄ |
| 8 | 3-(3-FC₆H₄)C₆H₄ | CH₂ | 4-OH—C₆H₄ |
| 9 | 3-(3-FC₆H₄)C₆H₄ | CH₂ | 2-(n-Bu)-imidazol-4-yl |
| 10 | 4-(2-FC₆H₄O)C₆H₄ | CH₂ | 2,3-Methylenedioxy-C₆H₃ |
| 22 | 3-indol-2-ylC₆H₄ | C(O) | C≡C—CH₃ |
| 23 | 4-benzimidazol-2-ylC₆H₄ | CH₂ | 3-MeO—C₆H₄ |
| 24 | 4-benzimidazol-2-ylC₆H₄ | CH₂ | 5-Et-furan-2-yl |
| 26 | 4-(2-FC₆H₄O)C₆H₄ | CH₂ | 2-HO-3-MeO—C₆H₃ |
| 27 | 2-(3-MeOC₆H₄)C₆H₄ | CH₂ | 2-HO-3-MeO—C₆H₃ |
| 28 | 3-(3-ClC₆H₄)C₆H₄ | CH₂ | 2-HO-3-MeO—C₆H₃ |
| 29 | 4-(2-FC₆H₄O)C₆H₄ | CH₂ | Et |
| 30 | 4-benzimidazol-2-ylC₆H₄ | CH₂ | 3-MeO—C₆H₄ |
| 33 | 3-(3-MeOC₆H₄)C₆H₄ | CH₂ | CH=C(Me)₂ |
| 38 | 4-(2-FC₆H₄O)C₆H₄ | CH₂ | Me |
| 39 | 4-(2-FC₆H₄O)C₆H₄ | — | 1-Et-piperidin-4-yl |
| 40 | 3-(3-FC₆H₄)C₆H₄ | CH₂ | 1-(i-Pr)-3,5-Me₂-pyrazol-4-yl |
| 41 | 2-PhO-pyridin-5-yl | CH₂ | Ph |
| 42 | 3-(3-ClC₆H₄)C₆H₄ | CH₂ | 1-Et-pyrazol-4-yl |
| 43 | 3-(3-FC₆H₄)C₆H₄ | CH₂ | 3,5,6-Me₃-pyrazin-2-yl |
| 45 | 4-(2-FC₆H₄O)C₆H₄ | CH₂ | 2-HO-5-MeO—C₆H₃ |
| 47 | 2-PhO-pyridin-5-yl | CH₂ | 5-Cl-thien-2-yl |
| 49 | 4-(2-FC₆H₄O)C₆H₄ | CH₂ | 4-HO-3-MeO—C₆H₃ |
| 51 | 2-(3-MeOC₆H₄)C₆H₄ | CH₂ | 3,5,6-Me₃-pyrazin-2-yl |
| 54 | 3-(3-FC₆H₄)C₆H₄ | CH₂ | 2-HO-3-MeO—C₆H₃ |
| 56 | 3-(3-FC₆H₄)C₆H₄ | CH₂ | 1-allyl-3-Me-pyrazol-4-yl |
| 58 | 3-(3-FC₆H₄)C₆H₄ | CH₂ | 1-Et-5-Me-pyrazol-4-yl |
| 60 | 4-(2-FC₆H₄O)C₆H₄ | CH₂ | 1-Et-pyrazol-4-yl. |

8. The method of claim 2, wherein the one of more compounds each comprise a combination mode of Ar¹, X, and R², said combination mode selected from the group consisting of:

| Combination Mode | Ar¹ | X | R² |
|---|---|---|---|
| 3 | 4-(2-FC₆H₄O)C₆H₄ | CH₂ | 2-OH-4-MeO—C₆H₃ |
| 4 | 2-(3-MeOC₆H₄)C₆H₄ | CH₂ | Quinolin-8-yl |
| 5 | 4-(Benzimidazol-2-yl)C₆H₄ | CH₂ | 2-MeO—C₆H₄ |
| 6 | 2-(3-MeOC₆H₄)C₆H₄ | CH₂ | 4-OH-3,5-Me₂—C₆H₂ |
| 39 | 4-(2-FC₆H₄O)C₆H₄ | — | 1-Et-piperidin-4-yl. |

9. The method of claim 3, wherein the one of more compounds each comprise a combination mode of Ar¹, X, and R², said combination mode selected from the group consisting of:

| Combination Mode | Ar¹ | X | R² |
|---|---|---|---|
| 22 | 3-indol-2-ylC₆H₄ | C(O) | C≡C—CH₃ |
| 23 | 4-benzimidazol-2-ylC₆H₄ | CH₂ | 3-MeO—C₆H₄ |
| 24 | 4-benzimidazol-2-ylC₆H₄ | CH₂ | 5-Et-furan-2-yl |
| 25 | 3-indol-2-ylC₆H₄ | C(O) | thiazol-5-yl |
| 30 | 4-benzimidazol-2-ylC₆H₄ | CH₂ | 3-MeO—C₆H₄ |
| 62 | 4-(Benzimidazol-2-yl)Ph | — | 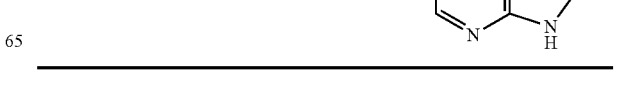 |
| 63 | 3-(Indol-2-yl)Ph | — | |
| 64 | 4-(2-F—PhO)Ph | — | |
| 65 | 3-(3-F—Ph)Ph | — | |
| 66 | 3-Br—Ph | — | |

10. The method of claim 3, wherein the one of more compounds each comprise a combination mode of Ar¹, X, and R², said combination mode selected from the group consisting of:

| Combination Mode | Ar¹ | X | R² |
|---|---|---|---|
| 22 | 3-indol-2-ylC$_6$H$_4$ | C(O) | C≡C—CH$_3$ |
| 23 | 4-benzimidazol-2-ylC$_6$H$_4$ | CH$_2$ | 3-MeO—C$_6$H$_4$ |
| 24 | 4-benzimidazol-2-ylC$_6$H$_4$ | CH$_2$ | 5-Et-furan-2-yl |
| 25 | 3-indol-2-ylC$_6$H$_4$ | C(O) | thiazol-5-yl |
| 30 | 4-benzimidazol-2-ylC$_6$H$_4$ | CH$_2$ | 3-MeO—C$_6$H$_4$ |
| 62 | 4-(Benzimidazol-2-yl)Ph | — | (4-Me-7H-pyrrolo[2,3-d]pyrimidin-4-yl) |
| 63 | 3-(Indol-2-yl)Ph | — | (4-Me-7H-pyrrolo[2,3-d]pyrimidin-4-yl) |
| 64 | 4-(2-F—PhO)Ph | — | (4-Me-7H-pyrrolo[2,3-d]pyrimidin-4-yl) |
| 65 | 3-(3-F—Ph)Ph | — | (4-Me-7H-pyrrolo[2,3-d]pyrimidin-4-yl) |

11. The method of claim 3, wherein the one of more compounds each comprise a combination mode of Ar¹, X, and R², said combination mode selected from the group consisting of:

| Combination Mode | Ar¹ | X | R² |
|---|---|---|---|
| 22 | 3-indol-2-ylC$_6$H$_4$ | C(O) | C≡C—CH$_3$ |
| 23 | 4-benzimidazol-2-ylC$_6$H$_4$ | CH$_2$ | 3-MeO—C$_6$H$_4$ |
| 25 | 3-indol-2-ylC$_6$H$_4$ | C(O) | thiazol-5-yl |
| 30 | 4-benzimidazol-2-ylC$_6$H$_4$ | CH$_2$ | 3-MeO—C$_6$H$_4$ |
| 62 | 4-(Benzimidazol-2-yl)Ph | — | (4-Me-7H-pyrrolo[2,3-d]pyrimidin-4-yl) |
| 63 | 3-(Indol-2-yl)Ph | — | (4-Me-7H-pyrrolo[2,3-d]pyrimidin-4-yl) |
| 65 | 3-(3-F—Ph)Ph | — | (4-Me-7H-pyrrolo[2,3-d]pyrimidin-4-yl) |

12. A method for treating an HIV infection in a host animal, the method comprising the step of administering to the host animal a therapeutically effective amount of one or more compounds of the formula or a pharmaceutically acceptable salt thereof; wherein the one of more compounds each comprise a combination mode of Ar¹, X, and R², said combination mode selected from the group consisting of:

| Combination Mode | Ar¹ | X | R² |
|---|---|---|---|
| 22 | 3-indol-2-ylC$_6$H$_4$ | C(O) | C≡C—CH$_3$ |
| 23 | 4-benzimidazol-2-ylC$_6$H$_4$ | CH$_2$ | 3-MeO—C$_6$H$_4$ |
| 24 | 4-benzimidazol-2-ylC$_6$H$_4$ | CH$_2$ | 5-Et-furan-2-yl |
| 25 | 3-indol-2-ylC$_6$H$_4$ | C(O) | thiazol-5-yl |
| 30 | 4-benzimidazol-2-ylC6H4 | CH$_2$ | 3-MeO—C$_6$H$_4$ | and one or more pharmaceutically acceptable carriers, excipients, or diluents, or combinations thereof.

13. A method for treating a coronavirus infection in a host animal, the method comprising the step of administering to the host animal a therapeutically effective amount of one or more compounds selected from the group consisting of:

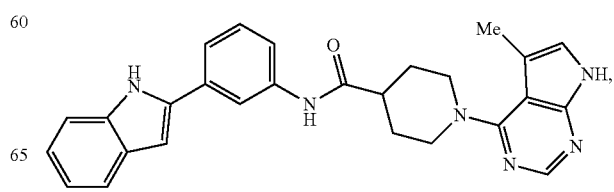

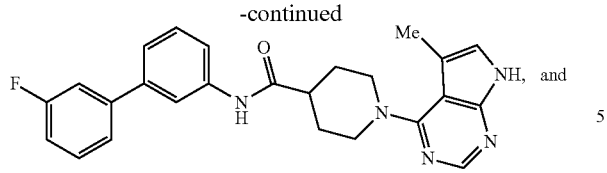
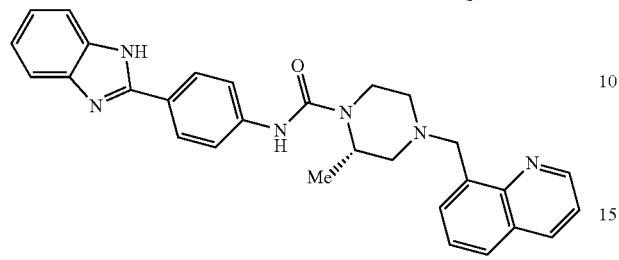
or a pharmaceutically acceptable salt thereof and one or more pharmaceutically acceptable carriers, excipients, or diluents, or combinations thereof.
* * * * *